US012305159B2

(12) United States Patent
Cimino et al.

(10) Patent No.: US 12,305,159 B2
(45) Date of Patent: *May 20, 2025

(54) TISSUE PROCESSING APPARATUS AND METHOD FOR PROCESSING ADIPOSE TISSUE

(71) Applicant: GID Bio, Inc., Louisville, CO (US)

(72) Inventors: William W. Cimino, Louisville, CO (US); Ramon Llull, Palma de Mallorca (ES); Adam J. Katz, Winston-Salem, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/391,490

(22) Filed: Dec. 20, 2023

(65) Prior Publication Data

US 2024/0279589 A1  Aug. 22, 2024

Related U.S. Application Data

(60) Continuation of application No. 18/077,947, filed on Dec. 8, 2022, now Pat. No. 11,898,138, which is a
(Continued)

(30) Foreign Application Priority Data

Sep. 5, 2013  (WO) ................ PCT/US2013/058292
Jan. 10, 2014  (WO) ................ PCT/US2014/011152

(51) Int. Cl.
*C12M 1/00*  (2006.01)
*A61K 35/32*  (2015.01)
(Continued)

(52) U.S. Cl.
CPC ............. *C12M 47/04* (2013.01); *A61K 35/32* (2013.01); *A61L 27/00* (2013.01); *C12M 45/02* (2013.01);
(Continued)

(58) Field of Classification Search
None
See application file for complete search history.

(56) References Cited

U.S. PATENT DOCUMENTS 3,854,704 A  12/1974  Balas
4,438,032 A  3/1984  Golde et al.
(Continued)

FOREIGN PATENT DOCUMENTS

EP  0512769 A2  11/1992
JP  2009189282 A  8/2009
(Continued)

OTHER PUBLICATIONS

Fodor et al.; Adipose Derived Stromal Cell (ADSC) Injections for Pain Management of Osteoarthritis in the Human Knee Joint; Aesthtic Surgery Journal; 2016; vol. 36(2); pp. 229-236.
(Continued)

*Primary Examiner* — Jyoti Nagpaul
(74) *Attorney, Agent, or Firm* — HOLZER PATEL DRENNAN

(57) ABSTRACT

A portable apparatus useful for collection and processing of human biological material, such as adipose or cancellous bone material, to prepare a concentrated product (e.g., stromal vascular fraction). The apparatus has a container with a containment volume with a tissue retention volume and a filtrate volume separated by a filter and with a pellet well for collecting concentrate product in the form of a pellet phase from centrifuge processing. The pellet well is accessible only from above when the apparatus is in an access orientation. Collected pellet phase material may be removed from the pellet well by direct aspiration, without suspending the material in a suspension liquid within the container. Access ports may be configured for access only from above the container. The apparatus may include a tissue collector disposed in the disuse retention volume to engage and
(Continued)

collect collagen or other stringy tissue. A method of processing adipose tissue to concentrate leuko stromal vascular cells includes multi-step processing using a portable container.

20 Claims, 14 Drawing Sheets

Related U.S. Application Data continuation of application No. 16/422,737, filed on May 24, 2019, now Pat. No. 11,649,427, which is a division of application No. 14/915,867, filed as application No. PCT/US2014/054373 on Sep. 5, 2014, now Pat. No. 10,336,980.

(60) Provisional application No. 61/926,148, filed on Jan. 10, 2014.

(51) Int. Cl.
*A61L 27/00* (2006.01)
*C12M 1/33* (2006.01)
*C12N 5/077* (2010.01)
*A61M 1/00* (2006.01)

(52) U.S. Cl.
CPC ........... *C12M 45/05* (2013.01); *C12N 5/0653* (2013.01); *A61M 1/892* (2021.05); *A61M 2202/08* (2013.01)

(56) References Cited

U.S. PATENT DOCUMENTS

| | | |
|---|---|---|
| 4,820,626 A | 4/1989 | Williams et al. |
| 5,035,708 A | 7/1991 | Alchas et al. |
| 5,226,914 A | 7/1993 | Caplan et al. |
| 5,330,914 A | 7/1994 | Uhlen et al. |
| 5,336,616 A | 8/1994 | Livesey et al. |
| 5,372,945 A | 12/1994 | Alchas et al. |
| 5,409,833 A | 4/1995 | Hu et al. |
| 5,443,438 A | 8/1995 | Wright et al. |
| 5,486,359 A | 1/1996 | Caplan et al. |
| 5,586,732 A | 12/1996 | Yamauchi et al. |
| 5,591,625 A | 1/1997 | Gerson et al. |
| 5,610,074 A | 3/1997 | Beritashvili et al. |
| 5,624,840 A | 4/1997 | Naughton et al. |
| 5,688,531 A | 11/1997 | Benayahu et al. |
| 5,728,739 A | 3/1998 | Ailhaud et al. |
| 5,736,396 A | 4/1998 | Bruder et al. |
| 5,786,207 A | 7/1998 | Katz et al. |
| 5,811,094 A | 9/1998 | Caplan et al. |
| 5,817,050 A | 10/1998 | Klein |
| 5,827,735 A | 10/1998 | Young et al. |
| 5,827,740 A | 10/1998 | Pittenger |
| 5,827,897 A | 10/1998 | Ailhaud et al. |
| 5,854,292 A | 12/1998 | Ailhaud et al. |
| 5,906,934 A | 5/1999 | Grande et al. |
| 5,908,784 A | 6/1999 | Johnstone et al. |
| 5,937,863 A | 8/1999 | Knowlton |
| 5,968,356 A | 10/1999 | Morsiani et al. |
| 6,200,606 B1 | 3/2001 | Peterson et al. |
| 6,261,549 B1 | 7/2001 | Fernandez et al. |
| 6,316,247 B1 | 11/2001 | Katz et al. |
| 6,391,297 B1 | 5/2002 | Halvorsen |
| 6,429,013 B1 | 8/2002 | Halvorsen et al. |
| 6,478,966 B2 | 11/2002 | Zhou et al. |
| 6,544,788 B2 | 4/2003 | Singh |
| 6,555,374 B1 | 4/2003 | Gimble et al. |
| 6,777,231 B1 | 8/2004 | Katz et al. |
| 6,841,150 B2 | 1/2005 | Halvorsen et al. |
| 6,852,533 B1 | 2/2005 | Rafii et al. |
| 7,001,746 B1 | 2/2006 | Halvorsen et al. |
| 7,033,587 B2 | 4/2006 | Halvorsen et al. |
| 7,078,230 B2 | 7/2006 | Wilkison et al. |
| 7,078,232 B2 | 7/2006 | Konkie et al. |
| 7,179,649 B2 | 2/2007 | Halvorsen |
| 7,266,457 B1 | 9/2007 | Hickman |
| 7,294,334 B1 | 11/2007 | Michal et al. |
| 7,361,368 B2 | 4/2008 | Claude et al. |
| 7,390,484 B2 | 6/2008 | Fraser et al. |
| 7,429,488 B2 | 9/2008 | Fraser et al. |
| 7,470,537 B2 | 12/2008 | Hedrick et al. |
| 7,473,420 B2 | 1/2009 | Fraser et al. |
| 7,501,115 B2 | 3/2009 | Fraser et al. |
| 7,514,075 B2 | 4/2009 | Hedrick et al. |
| 7,531,355 B2 | 5/2009 | Rodriguez et al. |
| 7,572,236 B2 | 8/2009 | Quick et al. |
| 7,582,292 B2 | 9/2009 | Wilkison et al. |
| 7,585,670 B2 | 9/2009 | Hedrick et al. |
| 7,595,043 B2 | 9/2009 | Hedrick et al. |
| 7,622,108 B2 | 11/2009 | Collins et al. |
| 7,641,643 B2 | 1/2010 | Michal et al. |
| 7,651,684 B2 | 1/2010 | Hedrick et al. |
| 7,659,118 B2 | 2/2010 | Furcht et al. |
| 7,670,596 B2 | 3/2010 | Collins et al. |
| 7,687,059 B2 | 3/2010 | Fraser et al. |
| 7,708,152 B2 | 5/2010 | Dorian et al. |
| 7,727,763 B2 | 6/2010 | McKenna, Jr. et al. |
| 7,732,190 B2 | 6/2010 | Michal et al. |
| 7,744,869 B2 | 6/2010 | Simon |
| 7,749,741 B2 | 7/2010 | Bullen et al. |
| 7,771,716 B2 | 8/2010 | Hedrick et al. |
| 7,780,649 B2 | 8/2010 | Shippert |
| 7,780,860 B2 | 8/2010 | Higgins et al. |
| 7,789,872 B2 | 9/2010 | Shippert |
| 7,794,449 B2 | 9/2010 | Shippert |
| 7,887,795 B2 | 2/2011 | Fraser et al. |
| 7,901,672 B2 | 3/2011 | Fraser et al. |
| 9,206,387 B2 | 12/2015 | Llull et al. |
| 9,260,697 B2 | 2/2016 | Cimino et al. |
| 9,296,984 B2 | 3/2016 | Cimino et al. |
| 9,907,883 B2 | 3/2018 | Llull et al. |
| 9,909,094 B2 | 3/2018 | Cimino et al. |
| 9,909,095 B2 | 3/2018 | Cimino et al. |
| 9,950,015 B2 | 4/2018 | Cimino et al. |
| 10,138,457 B2 | 11/2018 | Cimino et al. |
| 10,336,980 B2 | 7/2019 | Cimino et al. |
| 10,898,524 B2 | 1/2021 | Cimino et al. |
| 11,261,418 B2 | 3/2022 | Cimino et al. |
| 11,649,427 B2 | 5/2023 | Cimino et al. |
| 11,666,605 B2 | 6/2023 | Cimino et al. |
| 11,732,233 B2 | 8/2023 | Cimino et al. |
| 11,898,138 B2 * | 2/2024 | Cimino ................. A61L 27/00 |
| 2001/0030152 A1 | 10/2001 | Wright et al. |
| 2001/0033834 A1 | 10/2001 | Wilkison et al. |
| 2002/0076400 A1 | 6/2002 | Katz et al. |
| 2002/0119126 A1 | 8/2002 | Halvorsen |
| 2003/0082152 A1 | 5/2003 | Hedrick et al. |
| 2003/0161817 A1 | 8/2003 | Young et al. |
| 2003/0211602 A1 | 11/2003 | Atala |
| 2004/0067218 A1 | 4/2004 | Casteilla et al. |
| 2004/0097867 A1 | 5/2004 | Fraser et al. |
| 2004/0171146 A1 | 9/2004 | Katz et al. |
| 2005/0048034 A1 | 3/2005 | Fraser et al. |
| 2005/0076396 A1 | 4/2005 | Katz et al. |
| 2005/0153442 A1 | 7/2005 | Katz et al. |
| 2005/0282275 A1 | 12/2005 | Katz et al. |
| 2006/0051865 A1 | 3/2006 | Higgins et al. |
| 2006/0240546 A1 | 10/2006 | Goodwin et al. |
| 2007/0225665 A1 | 9/2007 | Perez-Cruet et al. |
| 2008/0014181 A1 | 1/2008 | Ariff et al. |
| 2008/0050275 A1 | 2/2008 | Bischof et al. |
| 2008/0319417 A1 | 12/2008 | Quijano et al. |
| 2009/0042267 A1 | 2/2009 | Park |
| 2010/0055087 A1 | 3/2010 | Higgins et al. |
| 2010/0285521 A1 | 11/2010 | Vossman et al. |
| 2010/0285588 A1 | 11/2010 | Stubbers et al. |
| 2011/0117650 A1 | 5/2011 | Riordan |

(56) References Cited

U.S. PATENT DOCUMENTS

| 2012/0003733 A1 | 1/2012 | Gueneron |
| 2012/0214659 A1 | 8/2012 | Do et al. |

FOREIGN PATENT DOCUMENTS

| JP | 2011125813 A | 6/2011 |
| JP | 2013507983 A | 3/2013 |
| WO | 2010100212 A1 | 9/2010 |
| WO | 2011052946 A2 | 5/2011 |
| WO | 2012006587 A2 | 1/2012 |
| WO | 2013106655 A1 | 7/2013 |
| WO | 2014039697 A1 | 3/2014 |
| WO | 2014110448 A1 | 7/2014 |

OTHER PUBLICATIONS

Garza et al.; "Use of Autologous Adipose-Derived Stromal Vascular Fraction to Treat Osteoarthritis of the Knee: A Feasibility and Safety Study"; Journal of Regenerative Medicine; 2015; vol. 4:1; 6 pgs.

Koh et al.; "Infrapatellar fat pad-derived mesenchymal stem cell therapy for kneee osteoarthritis"; The Knee; 2012; vol. 19; pp. 902-907.

Koh et al.; "Clinical results and second-look arthroscopic findings after treatment with adipose-derived stem cells for knee osteoarthritis"; Knee Surgery, Sports Traumatology, Arthroscopy; vol. 23(5); 2015; pp. 1308-1316; published online 2013.

Koh et al.; "Mesenchymal Stem Cell Injections Improve Symptoms of Knee Osteoarthritis"; Arthroscopy: The Journal of Arhtroscopic and Related Surgery; 2013; vol. 29(4); pp. 748-755.

Michalek et al.; "Autologous adipose tissue-derived stromal vascular fraction cells applicaiton in patients with osteoarthritis"; Cell Transplantation; Cognizant Communication Corporation; 2015; 36 pgs.

Pak; "Regeneration of human bones in hip osteonecrosis and human cartilage in knee osteoarthritis with autologous adipose-tissue-derived stem cells: a case series"; Journal of Medical Case Reports; 2011; vol. 5:296; 8 pgs.

Pak et al; "Safety reporting on implantation of autologous adipose tissue-derived stem cells with platelet-rich plasma into human articular joints"; BMC Musculoskeletal Disorders; 2013; vol. 14;337; 8 pgs.

Lindroos et al., "The Potential of Apidose Stem Cells in Regenerative Medicine," Stem Cell Rev and Rep (2011) 7:269-291, Springer Science+Business Media, LLC, published online Sep. 2010, pp. 269-291.

Pham et al., "Transplantation of Nonexpanded Adipose Stromal Vascular Fraction and Platelet-Rich Plasma for Articular Cartilage Injury Treatment in Mice Model," Hindawi Publishing Corporation, Journal of Medical Engineering, vol. 2013, 7 pgs.

Desando et al., "Intra-articular delivery of adipose derived stromal cells attenuates osteoarthritis progression in an experimental rabbit model," Arthritis Research & Therapy 2013, 16 pgs.

Toghraie et al., "Scaffold-free Adipose-derived Stem Cells (ASCs) Improve Experimentally Induced Osteoarthritis in Rabbits," Archives of Iranian Medicine, vol. 15, No. 8, Aug. 2012, pp. 495-499.

English et al., "A comparative assessment of cartilage and joint fat pad as a potential source of cells for autologous therapy development in knee osteoarthritis," Rheumatology Advance Access, published Sep. 2007, 8 pgs.

* cited by examiner

TISSUE PROCESSING APPARATUS AND METHOD FOR PROCESSING ADIPOSE TISSUE

CROSS-REFERENCE TO OTHER APPLICATIONS

This application of U.S. patent application Ser. No. 18/077,947 (published as U.S. Patent Application Publication No. 2023/0113828) entitled TISSUE PROCESSING APPARATUS AND METHOD FOR PROCESSING ADIPOSE TISSUE filed Dec. 8, 2022, which is a continuation of U.S. patent application Ser. No. 16/422,737 (published as U.S. Patent Application Publication No. 2019/0382710 and issued as U.S. Pat. No. 11,649,427) entitled TISSUE PROCESSING APPARATUS AND METHOD FOR PROCESSING ADIPOSE TISSUE filed May 24, 2019, which is a divisional of U.S. patent application Ser. No. 14/915,867 (published as U.S. Patent Application Publication No. 2016/0208211 and issued as U.S. Pat. No. 10,336,980) entitled TISSUE PROCESSING APPARATUS AND METHOD FOR PROCESSING ADIPOSE TISSUE having a 371(c) date of Mar. 1, 2016, which is a U.S. national stage filing under the Patent Cooperation Treaty of international patent application no. PCT/US2014/054373 (published as International Publication No. WO 2015/035221) filed Sep. 5, 2014, which claims a benefit of U.S. provisional patent application No. 61/926,148 entitled TISSUE PROCESSING APPARATUS AND METHOD FOR PROCESSING ADIPOSE TISSUE filed Jan. 10, 2014, the entire contents of each one and all of which are incorporated by reference herein for all purposes. This application, said U.S. patent application Ser. No. 18/077,974 (published as U.S. Patent Application Publication No. 2023/0113828), said U.S. patent application Ser. No. 16/422,737 (published as U.S. Patent Application Publication No. 2019/0382710 and issued as U.S. Pat. No. 11,649,427) and said U.S. patent application Ser. No. 14/915,867 (published as U.S. Patent Application Publication No. 2016/0208211 and issued as U.S. Pat. No. 10,336,980) claim priority pursuant to 35 U.S.C. §§ 119(a) and 365(b) to each of international patent application no. PCT/US2013/058292 (published as International Publication No. WO 2014/039697) entitled TISSUE PROCESSING APPARATUS AND METHOD FOR PROCESSING ADIPOSE TISSUE filed Sep. 5, 2013 and international patent application no. PCT/US2014/011152 (published as International Publication No. WO 2014/110448) entitled METHOD FOR PROCESSING CANCELLOUS BONE MATERIAL AND RELATED PRODUCTS, METHODS AND USES filed Jan. 10, 2014. The entire contents of each and every referenced U.S. patent application, U.S. patent, U.S. patent application publication, international patent application and international patent application publication identified above, or identified elsewhere herein, are incorporated herein by reference for all purposes.

FIELD OF THE INVENTION

The invention relates to apparatus and methods related to collection and processing human biological material, which processing may include preparation and/or recovery of a cell concentrate, for example a concentrate with leuko stromal vascular cells from adipose tissue or cancellous bone material.

BACKGROUND OF THE INVENTION

Adipose tissue is recognized as a promising source of stem cells with at least multi-potent differentiation potential. Lipoasperate obtained during a lipoplasty procedure, such as lipo surgery, may be processed to prepare a so-called stromal vascular fraction (SVF) that is rich in leuko stromal vascular cells, which include stem cells. Processing to prepare SVF may include washing lipoasperate with saline solution, followed by enzymatic digestion of washed tissue using collagenase, and centrifuging digested material to prepare SVF in the form of a centrifuged pellet. Such collection and processing of tissue involves several steps with transfer of contents between different process containers for different tissue collection and processing steps, which is cumbersome and provides significant opportunities for error or contamination.

Cancellous bone material is also a source of stem cells, and other stromal vascular fraction cells, which may be released from cancellous bone through enzymatic digestion similar to release of stromal vascular fraction cells through enzymatic digestion of adipose tissue.

Some attempts have been made to design portable containers in which lipoaspirate may be collected and then processed within the container to digest tissue and prepare a concentrate rich in leuko stromal vascular cells. Potential benefits of using such portable containers include a reduced need to transfer material between containers to perform different process steps and a reduction in the need for multiple, specially-designed processing containers. However, such multi-step processing in portable containers faces significant equipment and process design and operating limitations. Desired leuko stromal vascular cells, including stem cells, are sensitive to processing conditions and viability of recovered cells may suffer significantly if processing is not adequately controlled. Also, recovery of cells from the container is of critical importance. Significant potential exists for loss of valuable cells to recovery from the container, such as by cells adhering to internal equipment and surfaces within the container. One problem with multi-step processing in a single portable container is that the container design and processing operations must accommodate the different requirements of each of the different process steps to be performed in the single container, and with severe volume constraints in relation to a practical size for such a portable container. In contrast, processing systems that involve transfer of contents between multiple different containers for performance of different process steps benefit from an ability to optimize equipment and process design for each process container that is dedicated to performance of a single step of an overall process. Therefore, multi-container processing has significant advantages in terms of step-by-step equipment and process optimization. Moreover, a multi-container design is better suited for automation, for example with automated transfer of processed material through conduits between different process containers or with automated control of process parameters for uniformity and process control.

SUMMARY OF THE INVENTION

Disclosed are portable apparatus, uses of such apparatus and methods for processing of human biological material, and which biological material may contain stringy tissue, such as is the case with adipose tissue. Stringy tissue such as collagen adds additional complexity to an already complex processing situation, for example due to potential plugging of filters and interference with separation of desired cellular components. The apparatus and methods may be used to process biological material containing stringy tissue, but may also accommodate processing human biological material not containing any or any appreciable amount of stringy tissue, as may be the case for example with cancellous bone material, even though the description provided herein is primarily with reference to processing human biological material containing stringy tissue (e.g., adipose tissue). Processing may include applications to release and prepare a concentrate of portions of a biological material feed, for example to prepare a cell concentrate, and/or to selectively recover material of such a concentrate. In the context of adipose tissue and/or cancellous bone material, processing may be directed to preparing a concentrate product rich in targeted cells, for example leuko stromal vascular cells. Leuko stromal vascular cells may be referred to herein also as stromal vascular cells, stromal vascular fraction cells, or simply stromal cells. The description herein is provided with primary reference to processing adipose tissue to prepare a cell concentrate including cells released from adipose tissue, but the same discussion applies generally also to processing of cancellous bone material to prepare a cell concentrate including cells released from cancellous bone material.

Obtaining a high recovery in a concentrate of viable target cells, for example viable leuko stromal vascular cells, from adipose tissue or cancellous bone material and effective removal of such concentrate material of such a concentrate from the container in an operationally effective and convenient manner have been significant challenges for multi-step processing in a single container. In the case of adipose tissue in particular, the presence of stringy tissue components, such as collagen, complicates processing, and especially in the context of separating leuko stromal vascular cells for recovery in a concentrate at a high yield in a high quality concentrate product from a multi-step processing container. Even after preparation of such a cell concentrate in a multi-step processing container, removal of the cell concentrate material from the container is complicated by the presence of other materials that may remain in the container after preparation of the cell concentrate and possible physical loss of leuko stromal vascular cells, or other target cells, through adherence of cells to exposed surfaces within the container (e.g., surfaces of container walls, filters, mixers or other apparatus components disposed in the container). Container designs including a pellet well accessible from above, as disclosed herein, may permit effective and simplified processing to prepare in and remove from a portable multi-step processing container a target cell concentrate product material, for example a concentrate containing leuko stromal vascular cells.

A first aspect of the disclosure is provided by an apparatus for processing human biological material (e.g., adipose tissue or cancellous bone material) to prepare a cell concentrate. The apparatus has an access orientation. The access orientation may be a normal orientation of the apparatus when material is being added to or removed from the apparatus. The apparatus of the first aspect includes a container having an internal containment volume, the internal containment volume including a tissue retention volume and a filtrate volume. A filter is disposed within the internal containment volume with the tissue retention volume on one side of the filter and the filtrate volume on another side of the filter with the tissue retention volume and the filtrate volume being in fluid communication through the filter. An inlet port in fluid communication with the tissue retention volume is configured to access the tissue retention volume for introducing human biological material into the tissue retention volume. A suction port in fluid communication with the filtrate volume is configured to access the filtrate volume for suctioning material from the filtrate volume. The internal containment volume of the apparatus includes a pellet well disposed in a bottom portion of the filtrate volume below a bottom elevation of the filter and accessible only from above when the apparatus is in the access orientation. The pellet well may advantageously permit effective collection of a cell concentrate during centrifuge processing in the form of a pellet phase and uncomplicated post-collection selective removal of pellet phase material, such as by direct aspiration from the pellet well and without having to first suspend material of the pellet phase in a suspension liquid. The tissue retention volume may also be referred to as a retentate volume.

A number of feature refinements and additional features are applicable to the apparatus of the first aspect. These feature refinements and additional features may be used individually or in any combination. As such, each of the following features may be, but are not required to be, used with any other feature or combination of the first aspect or any other aspect of the disclosure.

The pellet well helps facilitate effective removal of pellet phase material by direct aspiration. The pellet well may be disposed in a bottom portion of the filtrate volume below a bottom elevation of the filter and accessible only from above when the apparatus is in an access orientation. Such a pellet well may be configured as a relatively deep, narrow chamber to help facilitate effective direct aspiration of pellet phase material, such as a concentrate of leuko stromal vascular cells or other cells.

The pellet well may include a second tapered portion, and also optionally a third tapered portion, of the internal containment volume below a first tapered portion of the internal containment volume, as described further below.

The filtrate volume may include a lower tapered portion below a bottom elevation of the filter and above a top elevation of the pellet well. The lower tapered portion of the filtrate volume may be defined by internal wall surfaces of the container that are each inclined relative to horizontal at a maximum angle of no larger than 60° when the container is in an access orientation. The lower tapered portion of the filtrate volume may be or include that portion of a first tapered portion of the internal containment volume, as noted above, that is located below the filter. At least a portion of the pellet well may be defined by a wall surface of the container inclined relative to horizontal at an angle that is larger than that maximum angle when the apparatus is in the access orientation. The wall surface of the container defining at least a portion of the pellet well may be inclined relative to horizontal at an angle of at least 70°, at least 75°, at least 80°, or at least 85°. The wall surface of the container defining at least a portion of the pellet well may be inclined relative to horizontal at an angle of 90° (vertical) or less than 90°, when the apparatus is in the access orientation.

The pellet well may have a volume in a range having a lower limit of 0.3 cubic centimeter, 0.5 cubic centimeter, 0.7 cubic centimeter, 0.8 cubic centimeter, 0.9 cubic centimeter or 1.0 cubic centimeter and an upper limit of 5 cubic centimeters, 3 cubic centimeters, 2 cubic centimeters, 1.5 cubic centimeters, or 1.3 cubic centimeters.

The pellet well may have a vertical height dimension when the apparatus is in an access orientation of at least 0.5 centimeter, 1 centimeter, at least 1.5 centimeters, at least 2 centimeters or at least 2.5 centimeters. The pellet well may have a vertical height dimension when the apparatus is in an access orientation of up to 10 centimeters, up to 5 centimeters, up to 4 centimeters, up to 3 centimeters or up to 2 centimeters.

The pellet well may have at least one portion with a vertical length of at least 0.5 centimeter or at least 1 centimeter; a maximum horizontal cross-dimension across the pellet well in that vertical length portion along the vertical length of no larger than 10 millimeters, no larger than 8 millimeters or no larger than 5 millimeters; and a minimum horizontal cross-dimension in that vertical length portion of no smaller than 2 millimeters or no smaller than 1.5 millimeters. As will be appreciated, the pellet well may have such a maximum horizontal cross-dimension (e.g., of no larger than 5 millimeters) and such a minimum horizontal cross-dimension (e.g., of no smaller than 1.5 millimeters) for a longer portion of the vertical height of the pellet well than a 1 centimeter, or a 0.5 centimeter vertical length portion. Having at least one such vertical length portion may facilitate receiving a distal end of a hypodermic needle or other aspiration tube in a relatively deep, narrow volume for aspiration of pellet phase material without significant premature breakthrough of less-dense aqueous liquid phase that may be disposed above the pellet phase following centrifuging. In some applications, such an aspiration tube (e.g., needle) may have an outer diameter of at least 1 millimeter. In some applications, the aspiration tube (e.g., needle) may have an outer diameter of no larger than 3 millimeters, no larger than 2.5 millimeters or no larger than 2 millimeters.

The internal containment volume of the container may have a tapered portion that tapers in a downward direction. The tapered portion may have a cross-sectional area that tapers, or reduces in size, in a direction toward the bottom of a collection volume. The tapered portion of the internal containment volume may help to direct and concentrate target dense material (e.g., dense cells, stromal vascular fraction) toward and into a collection volume disposed below a bottom elevation of the filter. At least a portion of the collection volume may be located within or below such a tapered portion. The pellet well may be disposed in a bottom portion of the collection volume. At least a part of the tapered portion may be located above the collection volume. The tapered portion of the internal containment volume may have a conical shape or any other shape with a cross-sectional area that tapers to reduce in size in a direction toward the bottom of the collection volume. In various implementations, at least a part of the tapered portion may be located above the collection volume. The tapered portion may have a uniform taper geometry (e.g., constant rate of taper) or may have a varying taper geometry (e.g., varying rate of taper in the direction of the taper).

In some implementations as noted above, the internal containment volume may have at least a first tapered portion and a second tapered portion that is located vertically lower than the first tapered portion, wherein the first tapered portion has a greater rate of taper than the second tapered portion. Such a first tapered portion may include the lower tapered portion discussed above. The first tapered portion may be defined at least in part by a first internal wall surface of the container that is at a first angle relative to horizontal when the apparatus is in an access orientation in a range having a lower limit of 20°, 25°, 30°, 35°, 40°, or 45° and an upper limit of 65°, 60°, 55°, or 50° and the second tapered portion may be defined at least in part by a second internal wall surface of the container that is at a second angle relative to horizontal when the apparatus is in an access orientation in a range having a lower limit of 50°, 60°, 65° or 70° and an upper limit of 89°, 88°, 85° or 82°, provided that the second angle is larger than the first angle. Such a first tapered portion, for example as viewed in a vertical plane cross-section, may be defined at least in part by opposing ones of such first internal wall surfaces. Such a second tapered portion in such a vertical cross-section may be defined at least in part by opposing ones of such second internal wall surfaces. The second tapered portion may be disposed partially or entirely within the filtrate volume. The second tapered portion may include at least a portion of a collection volume within the filtrate volume or may be entirely within such a collection volume. The second tapered portion may be or may be a part of the pellet well located in a bottom portion of such a collection volume. The volume within the second tapered portion of the internal containment volume may be in a range having a lower limit of from 0.2 percent, 0.3 percent, 0.5 percent, 0.7 percent or 0.8 percent of the portion of available processing volume of the container that is within the tissue retention volume and an upper limit of 2.5 percent, 2 percent, 1.5 percent, 1.2 percent or 1.1 percent of the portion of such available processing volume of the container that is within the tissue retention volume. Such a portion of the available processing volume within the tissue retention volume may be a volume capacity of the apparatus for human biological material feed (e.g., adipose tissue feed) that may be processed in the apparatus. For some implementations, the second tapered portion of the internal containment volume may have a volume in a range having a lower limit of 0.3 cubic centimeter, 0.5 cubic centimeter, 0.7 cubic centimeter, 0.8 cubic centimeter, 0.9 cubic centimeter or 1.0 cubic centimeter and an upper limit of 5 cubic centimeters, 3 cubic centimeters, 2 cubic centimeters, 1.5 cubic centimeters, or 1.3 cubic centimeters. The second tapered portion may have a vertical dimension when the apparatus is in an access orientation of at least 0.5 centimeter, at least 1 centimeter, at least 1.5 centimeters, at least 2 centimeters or at least 2.5 centimeters. The second tapered portion may have a vertical height dimension when the apparatus is in an access orientation of up to 10 centimeters, up to 5 centimeters, up to 4 centimeters or up to 3 centimeters. The internal containment volume may include a third tapered portion that is located below the second tapered portion that has a greater rate of taper than the second tapered portion. A third tapered portion may be defined at least in part by a third internal wall surface of the container that is at an angle relative to horizontal that is smaller than the second angle. The third angle may have a value as described previously for the first angle, provided that the second angle is larger than the third angle. The third tapered portion may occupy the lowermost portion of a collection volume in the filtrate volume, which may be a lowermost portion in the pellet well. The third tapered portion may have a vertical height dimension when the apparatus is in an access orientation that is smaller than a vertical height dimension of the second tapered portion. The third tapered portion may have such a vertical height dimension that is not larger than 1 centimeter, not larger than 0.5 centimeter or not larger than 0.3 centimeter. The third tapered portion may have a volume that is smaller than the volume of the second tapered portion. The third tapered portion may have a volume that is no larger than 0.5 cubic centimeter, no larger than 0.3 cubic centimeter or no larger than 0.2 cubic centimeter. The first tapered portion may have a vertical height dimension below a bottom of the filter that is smaller than a vertical height dimension of the second tapered portion, and such a vertical height dimension of the first tapered portion may be at least 0.5 centimeter or at least 1 centimeter. The first tapered portion may beneficially help stromal vascular fraction materials, or other target materials, to move into the second tapered portion when the apparatus is centrifuged. The second tapered portion, and also the third tapered portion if present, may be or be part of the pellet well.

Surprisingly, it has been found that the material of a pellet phase containing a concentrate of leuko stromal vascular cells, for example from adipose tissue or cancellous bone material, such as may be formed during centrifuging, may be directly aspirated from a collection volume at the bottom of the filtrate volume, and in particular from a pellet well at the bottom of the collection volume, without first removing overlying less-dense material phases and without dispersing the material of the pellet phase in a suspension liquid. Although the pellet phase may typically have a very high viscosity, it has been found that it is possible to aspirate the pellet phase material, for example though a hypodermic needle, without first diluting the pellet phase material to reduce viscosity, and without detrimental breakthrough of overlying, low viscosity aqueous liquid phase during the aspiration. This permits significant simplification in processing to remove such pellet phase material in some implementations.

In some implementations, the apparatus of the first aspect may include a tissue collector disposed in the tissue retention volume and rotatable relative to the container in at least a first direction of rotation about an axis of rotation, for example an axis of rotation of a rotatable shaft. The tissue collector may include at least one toothed member that sweeps through a portion of the tissue retention volume when the tissue collector is rotated in the first direction. The toothed member may be configured with a plurality of teeth to collect and retain stringy tissue when the tissue collector is rotated in the first direction in contact with human biological material containing the stringy tissue disposed in the tissue retention volume. Such a tissue collector may be preferred in applications involving processing of human biological material containing a significant amount of stringy tissue, such as for example in the case of processing adipose tissue. The stringy tissue may comprise collagen and/or other stringy tissue components, for example as is typically the case with lipoaspirate. The presence of stringy tissue presents a significant problem in relation to recovery of leuko stromal vascular cells from lipoaspirate, especially when processing large tissue volumes through multiple processing steps in a single container. Such stringy tissue may tend to collect on and clog a filter through which stromal vascular cells pass for collection. Problems with stringy tissue may be reduced to some degree by using a pre-filter upstream of the container to filter out stringy tissue before introduction into the container. However, such pre-filters are not easy to use and introduce additional complexity for the medical professional performing a lipoplasty operation. Also, even with the use of such a pre-filter, some stringy tissue may still be introduced into the container and may significantly impact cell collection in the container. The inclusion of a tissue collector in the container according may significantly reduce or even in some cases eliminate the need and complexity of using a separate pre-filter to remove some or all of the stringy tissue prior to introduction of tissue into the container for processing.

Each such toothed member may include at least 3, at least 4 or at least 5 teeth and may include an open space between the teeth of each pair of adjacent said teeth. Each such toothed member may include up to 10, up to 20 or up to 25 or more such teeth. A leading edge of a toothed member may be made up with at least 10 percent, at least 20 percent, at least 30 percent, at least 40 percent, at least 50 percent, at least 60 percent or more of open spaces. Such a leading edge of a toothed member may be made up of no more than 99 percent, 90 percent, 80 percent, 70 percent, 60 percent or 50 percent of teeth. By space on a leading edge of a toothed member made up of such open spaces, it is meant the space between tops of the teeth, and likewise the space on a leading edge made up of a toothed member refers to the space along the edge occupied by the tops of the teeth.

The tissue collector may include at least 1, at least 2, at least 3 or at least 5 such toothed members. The tissue collector may include up to 6, up to 10 or even more such toothed members. When the tissue collector includes multiple toothed members, some or all of such toothed members may have the same or a different configuration, for example in relation to member size, tooth design, number of teeth, teeth density, or other design features.

The apparatus may include at least 1 or at least 2 or more of such tissue collectors. The apparatus of the first aspect may include only 1, up to 2 or more such tissue collectors when the apparatus includes a plurality of tissue collectors two or more of the tissue collectors may be of the same configuration or of different configurations.

A toothed member may have a first end located radially toward the axis of rotation and a second end located radially away from the axis. Such a second end may be located a distance from the axis of at least 1 centimeter, at least 2 centimeters, at least 3 centimeters or at least 5 centimeters or more from the axis. Such second end may be located a distance from the axis of up to 6 centimeters, up to 8 centimeters, up to 10 centimeters or more from the axis.

Teeth may project toward a leading side, or edge, of the toothed member when the tissue collector is rotated in the first direction. Teeth may project in a plane of rotation of the toothed member when the tissue collector is rotated in the first direction. Teeth may have a height in a range having a lower limit of 1 millimeter, 2 millimeters, 3 millimeters or 5 millimeters and an upper limit of 20 millimeters, 15 millimeters or 10 millimeters relative to a bottom of an adjacent open space.

The apparatus of the first aspect may have one or more than one mixing impeller in the tissue retention volume. A mixing impeller may be configured to direct axial flow from the mixing impeller in a direction toward the tissue collector. Such a mixing impeller may include at least one portion configured to scrape a portion of the filter when the mixing impeller is operated. Each such portion of a mixing impeller configured to scrape a portion of the filter may include a peripheral edge portion of an impeller blade. At least a part of each such portion of the filter may be in a tapered portion of the filter that is disposed in a tapered portion of the internal containment volume. The tissue collector and such a mixing impeller may be coaxial and rotatable about a common axis of rotation. A spacing along such an axis between such a mixing impeller and a toothed member of the tissue collector may be at least 0.25 centimeter, at least 0.5 centimeter, at least 1 centimeter or at least 2 centimeters. A spacing along the axis between such a mixing impeller and a toothed member of the tissue collector may be up to 3 centimeters, up to 5 centimeters or even more. Such a mixing impeller may extend to a first radial distance from the axis and the tissue collector may extend to a second radial distance from the axis, with the second radial distance being larger than the first radial distance. Such a second radial distance may be at least 1 millimeter, at least 2 millimeters or at least 3 millimeters larger than such a first radial distance. Such a second radial distance may be no more than 3 centimeters, no more than 2 centimeters or no more than 1 centimeter larger than such a first radial distance.

In addition to such a mixing impeller, which may be a first mixing impeller, the apparatus of the first aspect may include one or more additional mixing impellers disposed in the tissue retention volume. The apparatus of the first aspect may include a second mixing impeller configured to direct axial flow in a direction away from the tissue collector when the rotatable shaft is rotated in the first direction. The tissue collector and such a second mixing impeller may be coaxial and rotatable about a common axis in the first direction. A spacing along an axis between such a second mixing impeller and a toothed member of the tissue collector may be at least 0.25 centimeter, at least 0.5 centimeter, at least 1 centimeter or at least 2 centimeters. A spacing along an axis between such a second mixing impeller and a toothed member of the tissue collector may be up to 3 centimeters, up to 5 centimeters or even more. Such a second mixing impeller may extend to a third radial distance from an axis that is at least 1 millimeter, at least 2 millimeters or at least 3 millimeters smaller than a radial distance from the axis to which the tissue collector may extend. Such a third radial distance may be no more than 3 centimeters, no more than 2 centimeters or no more than 1 centimeter larger than a radial distance to which the tissue collector may extend.

As noted above, the apparatus of the first aspect is orientable in an access orientation, also referred to as a first orientation or a collection orientation, in which the inlet port and the outlet port may be configured for access therethrough from above the container into the internal containment volume. The apparatus of the first aspect may preferably be configured to have all access to the internal containment volume be from above the container in the access orientation.

The apparatus of the first aspect may include an extraction port configured for accessing the internal containment volume to remove processed biological material from the internal containment volume, and in particular from the pellet well. Such an extraction port may be configured for access therethrough from above the container into the internal containment volume when the apparatus is oriented in a first orientation. Access through such an extraction port may be through a lumen extending through a rotatable shaft aligned with the axis.

The filter of the apparatus of the first aspect may have a separation size of at least 70 microns, at least 100 microns, at least 150 microns, at least 175 microns or at least 200 microns. The filter may have a separation size of no larger than 800 microns, no larger than 700 microns, no larger than 600 microns, no larger than 500 microns, no larger than 475 microns, no larger than 450 microns, no larger than 425 microns, no larger than 400 microns, no larger than 350 microns, no larger than 300 microns or no larger than 250 microns. In some preferred cell processing applications, the filter may have a separation size that is larger than 400 microns, for example for cell processing applications when the apparatus of the first aspect is to be used to a recover a stromal vascular fraction concentrate. Even though stromal vascular cells will easily pass through a 200 micron filter, the larger filter size may be advantageous to promote recovery of most or substantially all of the stromal vascular cells in the filtrate volume. Smaller size filters may plug to a degree that significantly reduces cell yield in terms of cell collection in and recovery from the filtrate volume, especially when processing material with stringy tissue content, such as adipose tissue. In some applications, however, the filter may have a separation size of 400 microns or less. By separation size, it is meant the size at which the filter effects separation between particles passing through and particles rejected by the filter during normal operation. The separation size may be determined by the size of openings provided in a surface filter, such as the mesh size of a mesh bag filter or of a rigid mesh screen filter.

The apparatus of the first aspect may be configured to be received in a centrifuge for centrifuging the container.

The apparatus of the first aspect may comprise human biological tissue comprising stringy tissue disposed in the tissue retention volume in contact with a toothed member of a tissue collector. The stringy tissue may comprise collagen. Tissue to be processed in the apparatus of the first aspect may comprise adipose removed from a patient during a lipoplasty procedure (e.g., lipoaspirate). For example, the term tissue may be used herein to refer to in-tact tissue, disrupted tissue, tissue fragments and biological fluids associated with or separate from tissue.

The apparatus of the first access may comprise cancellous bone material disposed in the internal containment volume for processing, with at least some of the cancellous bone material to be processed being disposed in the tissue retention volume.

The apparatus may be orientable in a collection orientation for collection of human biological material, or tissue, such as may comprise adipose tissue collected during a lipoplasty procedure or to collect cancellous bone material from a surgical procedure. The collection orientation is also referred to herein as an access orientation or a first orientation, and the terms are used interchangeably. For convenience of description except as noted, the apparatus is described as oriented in the access orientation. As such, relational references such as to top, bottom, up, down, above, below, elevations, vertical, horizontal and the like are in relation to the apparatus as oriented in the access orientation. The apparatus may be configured such that the apparatus may be stably supported in the access orientation. For example, the apparatus may have a base configured for interfacing with a flat, substantially horizontal surface (e.g., counter top or table top) to stably support the apparatus in the access orientation, or may be held in a mounting structure that maintains the apparatus in the access orientation. The apparatus may be advantageously configured to permit performance of many different operations with the apparatus when the apparatus is oriented in the access orientation.

The apparatus of the first aspect may be used in a variety of processing applications. The apparatus may, for example, be used for preparation of concentrated or separated portions of the collected human biological material, for example to produce a stromal vascular fraction rich in leuko stromal vascular cells, including stem cells, derived from adipose tissue or cancellous bone material. The apparatus has a design that accommodates retention of a target material (e.g., leuko stromal vascular cells) in a single container from collection through preparation of a desired product containing the target material. By target material, it is meant some component or components from or some portion or portions of collected human biological material of interest for recovery following processing in the apparatus, such as recovery in a concentrated or modified form relative to the collected human biological material (e.g., stromal vascular fraction concentrate rich in stem cells and/or rich in other leuko stromal vascular cells).

As noted above, the apparatus of the first aspect may include an extraction port in fluid communication with the internal containment volume and configured for removing processed biological material from the internal containment volume. Any or all of the inlet port, the suction port and the extraction port may be configured for access therethrough from above the container into the internal containment volume. The extraction port may be located above a portion of the filter, so that the advancing tip of a hypodermic needle pierces the filter when the tip of the hypodermic needle is advanced from the extraction port into the collection volume. The collection volume may include a nadir (in the pellet well) and the extraction port may be positioned above the nadir so that the tip of a hypodermic needle inserted through the extraction port may be advanced vertically downward to the vicinity of the nadir of the collection volume.

The apparatus of the first aspect may be configured for advancing a hypodermic needle through a lumen and out of the distal end of the lumen to access the collection volume, and in particular the pellet well, with an advancing tip of the hypodermic needle. The distal end of the lumen may be located in the tissue retention volume above a portion of the filter, so that the advancing tip of the hypodermic needle may pierce and pass through the filter when the tip of the hypodermic needle exits the distal end of the lumen and is advanced from the distal end of the lumen into the collection volume. The collection volume may include a nadir (in the pellet well), and an axis of the lumen may be aligned so that the tip of a hypodermic needle exiting the distal end of the lumen may be advanced to the vicinity of the nadir of the collection volume. The hypodermic needle may thus access the collection volume, and in particular the pellet well, to permit aspiration of material from the collection volume (e.g., aspiration of stromal vascular fraction concentrate or other processed biological material collecting in the pellet well during processing).

As noted, the suction port is in fluid communication with the filtrate volume. By the suction port being in fluid communication with the filtrate volume, it is meant that the suction port is fluidly connected directly to the filtrate volume, and not indirectly through the tissue retention volume and the filter. The fluid communication may be provided by a dedicated conduit extending from the suction port to a desired location within the filtrate volume where it is desired to apply suction directly to the filtrate volume.

The apparatus of the first aspect may include multiple suction ports.

Any one or more of the inlet port, the suction port of other ports providing access to the internal containment volume may be configured for access through the port from above. In this way, access through each such port may be conveniently from above the apparatus, providing a significant advantage to a user of the apparatus in that such a user may focus all access manipulations from above the apparatus while the apparatus is in a normal position in the collective orientation, for example with the apparatus freestanding on a flat work surface such as a table or counter. Although such access from above the container may be at some angle relative to vertical, in a preferred implementation the access through such port is in a vertical direction from above the container. In one preferred implementation, all access to the internal containment volume may be through access ports wherein each such access port (e.g., inlet port, suction port, extraction port, other ports) is configured for access through the access port only from above the container. In another preferred implementation, all access ports may be configured for access through each such access port in a vertical direction from above the container.

The apparatus of the first aspect may be configured with a very convenient size from a number of perspectives, and with efficient use of the internal containment volume to facilitate efficient collection of biological material and versatility in post-collection processing. The apparatus may be sized for convenient hand transportation, such as between a location where human biological material may be collected to other, different locations, where various processing of collected material may be carried out. The apparatus may also be sized for convenient manipulation by a person.

For many applications, the apparatus of the first aspect may be sized and configured such that the internal containment volume has a volume in a range with a lower limit of 6 cubic centimeters, 12 cubic centimeters, 30 cubic centimeters, 40 cubic centimeters, 100 cubic centimeters, 200 cubic centimeters, 250 cubic centimeters, 300 cubic centimeters, 500 cubic centimeters, 600 cubic centimeters or 700 cubic centimeters and an upper limit of 1500 cubic centimeters, 1300 cubic centimeters, 1100 cubic centimeters, 1000 cubic centimeters, 900 cubic centimeters, 800 cubic centimeters, 500 cubic centimeters, 400 cubic centimeters or 300 cubic centimeters, provided that the upper limit is larger than the lower limit. One preferred range for some applications is for the internal containment volume to be in a range of 700 cubic centimeters to 1000 cubic centimeters. Another preferred range for some applications is for the internal containment volume to be within a range of from 75 cubic centimeters or 100 cubic centimeters to 500 cubic centimeters or to 400 cubic centimeters, such as for example to prepare a concentrate of leuko stromal vascular cells for administration to the vicinity of a joint for treatment of osteoarthritis. By internal containment volume, it is meant the total internal volume contained within the walls defining the container, including volume that is occupied by internal hardware, such as for example may be occupied by a mixing device, suction conduits, barrier skirt, etc. As will be appreciated, less than all of the internal containment volume will be available for processing within the internal containment volume.

The terms "available processing volume" or "useful volume" or "internal processing volume" are used interchangeably herein to refer to the portion of the internal containment volume that is effectively available to receive and process human biological material and additives (e.g., wash other additives) during use of the apparatus of the first aspect for collection of biological material or for post-collection processing. This available processing volume is equal to the internal containment volume less portions of the internal containment volume occupied by hardware (e.g., mixing device, filter, skirt, suction tubes, barrier member, etc.) and less unoccupied portions of the internal containment volume not effectively accessible for occupation by biological material during collection operations or by biological material or additives during post-collection processing. For example, the available processing volume may exclude a small volume at the top of the container that is above a bottom extension of the inlet port into the internal containment volume. This small void space may be beneficial to permit space for fluid to slosh within the container when contents of the container may be internally mixed or externally agitated (e.g., by a shaker table). For many applications, the available processing volume may be in a range having a lower limit of 5 cubic centimeters, 10 cubic centimeters, 20 cubic centimeters, 25 cubic centimeters, 50 cubic centimeters, 75 cubic centimeters, 100 cubic centimeters, 200 cubic centimeters, 300 cubic centimeters, 400 cubic centimeters, 500 cubic centimeters, 600 cubic centimeters, 650 cubic centimeters or 700 cubic centimeters and an upper limit of 1300 cubic centimeters, 1100 cubic centimeters, 1000 cubic centimeters, 900 cubic centimeters, 850 cubic centimeters, 800 cubic centimeters, 750 cubic centimeters, 700 cubic centimeters, 600 cubic centimeters, 500 cubic centimeters, 400 cubic centimeters, 350 cubic centimeters, 300 cubic centimeters, 250 cubic centimeters or 200 cubic centimeters, provided that the upper limit is larger than the lower limit.

Advantageously, the apparatus of the first aspect may be configured so that a large portion of the available processing volume is within the tissue retention volume, while still permitting a high level of performance for various processing operations. The tissue retention volume may comprise at least 40 percent, at least 50 percent, at least 60 percent, at least 65 percent or at least 70 percent of the available processing volume with the container. Often, the tissue retention volume will comprise not more than 95 percent, not more than 90 percent or not more than 85 percent of the available processing volume. For many preferred implementations, the tissue retention volume may comprise a portion of the available processing volume that is at least 3 cubic centimeters, at least 5 cubic centimeters, at least 10 cubic centimeters, at least 25 cubic centimeters, at least 50 cubic centimeters, at least 100 cubic centimeters, at least 200 cubic centimeters, at least 300 cubic centimeters, at least 400 cubic centimeters, at least 500 cubic centimeters, at least 600 centimeters or at least 650 cubic centimeters. The apparatus may advantageously be configured with only a small portion of the available processing volume occupied by a collection volume, located below the filter. For example, the collection volume may comprise no more than 10 percent, no more than 7 percent or no more than 5 percent of the available processing volume.

The portable container apparatus may be configured to facilitate effective processing of a wide range of human biological material (e.g., adipose tissue, cancellous bone material) volumes and that may be compatible with a large number of common centrifuges in some preferred applications. When in the access orientation, the internal containment volume may include a first portion that is cylindrical or is frustoconical tapering toward the bottom of the internal containment volume with an angle of taper relative to horizontal at a first angle; a second portion disposed below the first portion, the second portion being frustoconical tapering toward the bottom of the internal containment volume with an angle of taper relative to horizontal at a second angle; and a third portion disposed below the second portion in the pellet well, the third portion being cylindrical or frustoconical tapering toward the bottom of the internal containment volume at an angle of taper relative to horizontal at a third angle, with the first angle and the third angle being larger than the second angle. The first angle and the third angle may each independently be at least 70°, at least 75°, at least 80°, or at least 85°. The second angle may be in a range having a lower limit of 30°, 40°, 42° or 45° and an upper limit of 60°, 55°, 50°, 48° or 45°, provided the upper limit is higher than the lower limit. The second angle may be about 45° in some preferred implementations.

The internal containment volume may be defined at least in part by a shell. The portable container apparatus may have some preferred dimensions in some implementations. The shell may have a cross-section, which may preferably be a circular cross-section, configured to fit within a centrifuge receptacle (e.g., centrifuge bucket) for centrifuging the portable container apparatus. The shell, a portion of the shell configured to be received in a centrifuge receptacle, the internal containment volume and/or a portion of the internal containment volume configured to be received in a centrifuge receptacle may have a maximum cross-section taken horizontally through the shell that may be fit entirely within a circle with a diameter not larger than 16 centimeters, not larger than 14 centimeters, not larger than 12 centimeters, not larger than 10 centimeters, not larger than 8 centimeters or not larger than 7 centimeters. Any such maximum cross-section may be such as to not fit entirely within a circle having a diameter of not smaller than 2 centimeters, not smaller than 3 centimeters, not smaller than 4 centimeters or not smaller than 6 centimeters. The shell, a portion of the shell configured to be received in a centrifuge receptacle, the internal containment volume and/or a portion of the internal containment volume configured to be received in a centrifuge receptacle may have a height dimension in a range having a lower limit of 2 centimeters, 3 centimeters, 4 centimeters, 5 centimeters or 6 centimeters and an upper limit of 16 centimeters, 14 centimeters, 12 centimeters, 10 centimeters, 8 centimeters or 7 centimeters. The portable container apparatus may have a total height in a range having a lower limit of 2 centimeters, 3 centimeters, 4 centimeters, 6 centimeters and 8 centimeters and an upper limit of 26 centimeters, 23 centimeters, 20 centimeters, 17 centimeters, 14 centimeters or 12 centimeters. The portable container apparatus may have an internal processing volume in a range of from 5 cubic centimeters, 10 cubic centimeters, 20 cubic centimeters, 50 cubic centimeters, 100 cubic centimeters, 150 cubic centimeters or 200 cubic centimeters and an upper limit of 400 cubic centimeters, 350 cubic centimeters, 300 cubic centimeters, or 200 cubic centimeters, with the upper limit being larger that the lower limit.

One significant area of medical application for use of the apparatus of the first aspect is to prepare cell concentrate, for example leuko stromal vascular cell concentrate, for use in the treatment of osteoarthritis, for example in the vicinity of a patient's joint. In some applications for treatment of osteoarthritis, the apparatus may be configured with a relatively small internal containment volume designed to process a volume of adipose tissue or cancellous bone material to prepare a volume of leuko stromal vascular cells that may be appropriate for use in a single injection formulation for treatment of osteoarthritis at a joint. In some implementations, the apparatus may have an internal containment volume with a volume in a range having a lower limit of 35 cubic centimeters, 50 cubic centimeters, 75 cubic centimeters, 100 cubic centimeters, 125 cubic centimeters, 150 cubic centimeters, 200 cubic centimeters or 250 cubic centimeters and an upper limit of 400 cubic centimeters, 350 cubic centimeters or 300 cubic centimeters. In some implementations, the apparatus may be designed with a tissue retention volume that includes a portion of the available processing volume of the apparatus in a range having a lower limit of 25 cubic centimeters, 50 cubic centimeters, 75 cubic centimeters or 100 cubic centimeters and an upper limit of 250 cubic centimeters, 200 cubic centimeters 150 cubic centimeters or 125 cubic centimeters, with the upper limit being larger than the lower limit. The apparatus may have a tissue retention volume comprising a portion of the available processing volume in a range having a lower limit of 40%, 45% or 48% and an upper limit of 60%, 55% or 52% of the total available processing volume, and with the remainder of the available processing volume preferably within the filtrate volume. Having an available processing volume split about equally between the tissue retention volume and the filtrate volume permits washing a maximum volume of human biological material (e.g., adipose tissue) that may be disposed in the tissue retention volume with a volume ratio of wash liquid to adipose tissue of 1:1. The apparatus may be designed to collect a pellet phase volume, which may correspond with a pellet well volume, in a range of from 0.5 cubic centimeter, 0.75 cubic centimeter or 1 cubic centimeter and an upper limit of 2.5 cubic centimeters, 2 cubic centimeters 1.5 cubic centimeters or 1.3 cubic centimeters. The apparatus may include the pellet well having a volume in a range as a percentage of the portion of the available processing volume within the tissue retention volume that has a lower limit of 0.2%, 0.3% or 0.5% and an upper limit of 2%, 1.5% or 1%.

The apparatus of the first aspect may be packaged within a hermetic enclosure, for example as packaged for transportation and storage prior to use. The apparatus may be sterilized prior to packaging and maintained in a sterile environment within the hermetic enclosure at least until the apparatus is removed from the hermetic enclosure for use. The apparatus may be designed for a single use following removal from the hermetic enclosure. After such single use, the apparatus may be disposed of in an appropriate manner.

A second aspect of the disclosure is provided by a method using an apparatus of the first aspect, and including direct aspiration of material of a pellet phase from the pellet well. Such direct aspiration may include selectively removing material of the pellet phase from the container. The container of the apparatus may contain density-separated phases following enzymatic digestion of human biological material, with the density-separated phases including lower-density material phases and a higher-density pellet. The selectively removing may include inserting an aspiration needle from the outside to the inside of the container to contact the pellet phase inside the container without suspending material of the pellet phase in a suspension in the container. The second aspect may include processing adipose tissue or cancellous bone material to concentrate leuko stromal vascular cells associated with the adipose tissue or cancellous bone material. The method may combine particular processing in combination with a portable container of an apparatus for processing human biological material containing stringy tissue, to address significant design constraints associated with the use of portable containers for multi-step processing of adipose or other tissue. The method of the second aspect may include multi-step processing within the portable container of the apparatus of the first aspect. Multi-step processing may include washing the adipose tissue within the container to remove contaminants from the adipose tissue. After the washing, the method may include digesting adipose tissue within the container (e.g., containing collagenase), with the digesting comprising adding to the container a volume of enzyme-containing digestion medium to contact washed adipose tissue in the container. After permitting enzymatic digestion in the container for a retention time following adding the digestion medium, the method may include disposing the container in a centrifuge and centrifuging the container in the centrifuge to form density-separated phases within the container, the density-separated phases including lower-density material phases and a higher-density pellet phase comprising leuko stromal vascular cells. After the centrifuging, the method may include selectively removing material of the pellet phase from the container.

The method of the second aspect particularly addresses processing within the constrained context of multiple-step processing within a single portable container. The method may permit effective processing within such a portable container in a manner to address inherent equipment and processing design problems associated with multi-step processing in portable containers and without excessive losses of cell viability or physical losses of cells to adherence to equipment and container surfaces inside the container.

A number of feature refinements and additional features are applicable to the second aspect of the invention. These feature refinements and additional features may be used individually or in any combination. As such, each of the following features may be, but are not required to be, used with any other feature or combination of the second aspect or any other aspect of the disclosure.

The method may include, after centrifuging, removing the container from the centrifuge prior to the selectively removing.

Aspirating the material of the pellet phase without first suspending the material in a suspension liquid is referred to herein as direct aspiration of the material of the pellet phase. Such direct aspiration may be performed without removal of lower-density material phases from above the pellet phase, may be performed after removing some but not all of the lower-density material phases or may be performed after removing all of the lower-density material phases. The lower-density material phases may include an aqueous phase above the pellet phase and prior to the aspirating, the lower-density aqueous phase may be not removed from above the pellet phase. Such aqueous phase may be left substantially in-tact within the container during the aspirating, and may remain in the container following the aspirating. Some or all of the lower-density material phases may remain in the container after the aspirating. The inserting may comprise inserting the aspiration tube downward into the container from above. When lower-density material phases remain in the container during the aspirating, the aspiration tube may be inserted downwardly through the lower-density material phases and into the pellet phase material located below the lower-density material phases. The aspiration tube may be a needle (e.g., hypodermic needle), cannula or other device with a fluid communication channel. For many applications, an 18 to 22 gauge hypodermic needle may be used for the aspiration tube. During the aspirating, the aspiration tube may be in fluid communication with a fluid receptacle, and the aspirating may include collecting at least a majority of the material of the pellet phase in the fluid receptacle. Such a fluid receptacle may be a syringe or other fluid containment apparatus. By selectively removing the material of the pellet phase without requiring prior removal of less-dense material phases above the pellet phase, the process operation of removing the pellet phase material may be considerably simplified and the potential for processing errors and for loss of cells to adhesion to apparatus surfaces may be significantly reduced. The fluid receptacle may be pre-loaded with a dispersion medium that mixes with the material of the pellet phase in the fluid receptacle when the dispersion material is introduced into the fluid receptacle during the aspirating. The dispersion medium may be a liquid medium to disperse and suspend the cells of the pellet phase material. The dispersion medium may be a gel or gel-like material in which the cells of the pellet phase material may disperse and be retained. The dispersion medium may be a delivery vehicle for the cellular material (e.g., leuko stromal vascular cells) of the pellet phase, and such cellular material may be administered to a patient in a delivery composition including the cellular material and the dispersion medium. Some examples for a dispersion medium that may be preloaded into the fluid receptacle include compositions that may be or include one or more of the following, either alone or with other components: saline solution (e.g., a balanced saline solution, Hank's Balanced Solution), crystalloid solution (e.g., Lactated Ringer's solution), hyaluronic acid and hyaluronic acid-based materials. Such hyaluronic acid-based materials may be substrate or carrier compositions based on hyaluronic acid. Any of these listed materials for possible use as or inclusion in a dispersion medium may also be part of a final delivery composition for administration to a patient. The volume of dispersion medium pre-loaded into the fluid receptacle may be any convenient volume for the application. In some preferred implementations, the dispersion medium may be present in a sufficient volume to prevent clumping of material of the pellet phase in the fluid receptacle. The dispersion medium in the fluid receptacle may have a volume such that a volume ratio of the volume of the dispersion medium to the volume of the pellet phase material introduced into the fluid receptacle during the aspirating is at least 1:1, at least 2:1, or at least 3:1. Often, such a volume ratio may be up to 10:1, up to 7:1, up to 5:1; up to 3:1 or up to 2:1. In some implementations, the dispersion medium in the fluid receptacle may have a volume of at least 1 milliliter, at least 2 milliliters or at least 3 milliliters. In some implementations, the dispersion medium in the fluid receptacle may have a volume of up to 10 milliliters, up to 7 milliliters, up to 5 milliliters, up to 3 milliliters or up to 2 milliliters. A mixture formed in the fluid receptacle during the aspirating may be further processed to prepare a delivery composition including material of the pellet phase or the mixture may be in the form of a delivery composition that is ready as prepared in the fluid receptacle for direct administration to a patient, such as by direct injection from the fluid receptacle into the patient following completion of the aspirating. Further processing may include centrifuging the mixture formed in the fluid receptacle to reform a pellet phase, separation of the pellet phase material from other, typically less-dense material phases, that form during the centrifuging, followed by formulation of the pellet phase with other components to prepare a desired delivery composition, which could include any of the components that could be used as the dispersion medium or any other components suitable for a delivery composition. When the delivery composition is to be injected into a joint to treat osteoarthritis, the delivery composition may in some preferred implementations have a total volume in a range having a lower limit of 0.5 milliliter, 1 milliliter or 2 milliliters and an upper limit of 5 milliliters, 4 milliliters or 3 milliliters. The delivery composition may include a volume of the pellet phase material in a range having a lower limit of 0.25 milliliter, 0.5 milliliter, 0.75 milliliter, or 1 milliliter and an upper limit of 2.5 milliliters, 2 milliliters or 1.5 milliliters. When the pellet phase material includes a concentrate of leuko stromal vascular cells, the delivery composition will include a mixture of the different cells present in the leuko stromal vascular fraction, without purification and without culturing. This is distinguishable from other treatment compositions that may be prepared using only certain types of cells separated from the leuko stromal vascular fraction mixture or using cultured cells.

In some implementations, selective removal of material of the pellet phase may involve removing one or more, or all, of the lower-density material phases layers prior to removing material of the pellet phase from the container. When lower-density material phases may be removed prior to removal of material of the pellet phase, removing the lower-density material phases may include removing such lower-density material phases from the container in sequence of increasing density, which may include suctioning the lower-density material phases from the container through open end of a suction conduit disposed in the container. Preferably, such an open end of a suction conduit may be disposed in the container not directly above the pellet phase, to reduce the possibility that suction created in the container would structurally disrupt the pellet phase. In some preferred implementations, the pellet phase remains in place and stationary, relative to the container, while the lower-density material phases are removed. In some implementations, removing the lower-density material phases may include tipping the container during suctioning of lower-density material phases to promote flow of at least a final suction portion of the lower-density material phases within the container laterally away from the pellet and toward the open end of the suction conduit. The container may include a corner located lateral to the pellet phase, and which may be located at an elevation of the container that is higher than the bottom elevation of the pellet phase, or even higher than a top elevation of the pellet phase. The tipping may promote flow of fluid of the lower-density material phases laterally toward the corner for suctioning from the vicinity of the corner into the open end of the suction conduit. In some preferred implementations, the lower-density material phases may be removed through a top of the container.

The method may include one or more steps other than or in addition to any or any combination of the steps noted above. Any such other or additional step may be performed between any of the steps noted above or may be performed prior to or after any of the steps noted above.

After the selectively removing, the pellet phase material removed from the container may be further processed and/or mixed with other components as desired, for example to prepare a desired delivery composition for administration to a patient. When the pellet phase material is first suspended in suspension liquid in the container before removal, the further processing may include centrifuging the mixture, recovering the pellet phase material and formulating the pellet phase material to prepare a delivery composition. Such a delivery composition may be or have features as described above.

The digesting may include continuous agitation of the contents during some portion or substantially all of the retention time during the digesting. The agitation may include mixing, periodically or continuously, with a rotatable mixer disposed within the container.

The washing may include at least one wash cycle, which may involve only a single wash cycle or multiple wash cycles (at least two).

Each wash cycle may comprise removing wash liquid (preferably at least a majority of the wash liquid and more preferably substantially all of the wash liquid) by suctioning from the filtrate volume of the container on the first side of the filter. During such suctioning, the wash liquid may be removed through a top of the container.

Mixing the wash liquid may include operating a rotatable mixer disposed in the container. The rotatable mixer may be manually operable, such as by a handle attached to a rotating shaft disposed through a top of the container. Such a rotatable mixer may also be used to mix the digestion medium and the adipose tissue following addition of the digestion medium to the container, and preferably shortly after such addition, to thoroughly mix the digestion medium and washed adipose tissue to be digested.

The wash liquid used during the washing may but need not be of the same composition for each wash cycle. The wash liquid may include one or more additives. For example the wash liquid for one of more of the wash cycles may include one or more than one of an anti-clotting agent, an antibiotic and an antifungal.

The method may include adding a stopping reagent to the container to stop enzymatic activity within the container. The stopping reagent may comprise human albumin.

The container may be conveniently transported between different locations for performance of different processing at the different locations, and preferably may be manually transported by being carried by a person.

The method permits convenient and controlled processing of significant quantities of adipose tissue or cancellous bone material in a convenient manner.

It should be appreciated that when reference is made to "adipose tissue" or a volume thereof in relation to a method of the invention the reference may be to in-tact adipose tissue and any associated contaminants that are present with the in-tact tissue. These contaminants come from the biological materials extracted from subjects to obtain the adipose tissue. Contaminants that may be associated with the adipose tissue include for example blood, free lipids, small particles and debris and other materials that may have been collected with the adipose tissue or result from degradation during tissue collection or processing operations. The amounts of these contaminants will generally be higher in unwashed adipose tissue at the commencement of washing operations and will generally be lower at the commandment of digesting operations, following the washing.

It should be appreciated that when reference is made to "cancellous bone material" or a volume thereof in relation to a method of the disclosure the reference may be to cancellous bone and associated non-bone material as removed from a patient or as initially disposed in the portable container apparatus, or to any portion or component of such material that is present in the portable container apparatus at any time during processing. Non-bone material in the cancellous bone material may be from biological materials extracted from subjects along with cancellous bone. Non-bone material that may be associated with cancellous bone may include for example bone marrow, blood, and other blood-derived tissues and fluids that may have been collected with cancellous bone or that result from degradation during tissue collection or during processing operations. The amounts of these non-bone components will generally be higher in unwashed cancellous bone material at the commencement of washing operations and will generally be lower at the commencement of digesting operations, following the washing. Immediately prior to the washing, the cancellous bone material within the retentate volume may comprise non-bone material including bone marrow and other blood-derived tissues and fluids. During the washing, at least a majority, and preferably all or almost all, of the bone marrow and other blood-derived tissues and fluids may be washed from the cancellous bone material and removed from the filtrate volume. At least a majority, and preferably all or almost all, of the calcified bone component of the cancellous bone material may be retained in the retentate volume throughout the washing. In some implementations, at least a majority, and preferably all or almost all, of the calcified bone component of the cancellous bone material may be retained in the retentate volume throughout the washing, digesting and centrifuging.

A third aspect of the disclosure is provided by uses of concentrate of from adipose tissue and/or from cancellous bone material for treatment of osteoarthritis. The cells may, for example include stem cells. The cells, for example, may include leuko stromal vascular cells.

A treatment composition for use to treat osteoarthritis may comprise a concentrate of a mixture of leuko stromal vascular cells as recovered from processing of adipose tissue, for example without purification of a specific cell type or cell types from the stromal vascular fraction mixture and without culturing cells. The composition may be or include any delivery composition or feature thereof described in relation to the second aspect or any other aspect of the disclosure.

A method for treating osteoarthritis may include administration to a patient of such a treatment composition. The administration may involve injection of the treatment composition into or in the vicinity of a joint to be treated for osteoarthritis. The administration may be by injection from a fluid receptacle (e.g., syringe) into which pellet phase material is directly aspirated and in which the treatment composition was prepared to include dispersion medium pre-loaded into the fluid receptacle, for example as described above.

DETAILED DESCRIPTION OF PREFERRED EMBODIMENTS

The following description of embodiments may be exemplified by reference to collecting and processing tissue comprising adipose, but the principles described generally apply also to collection and processing of other tissue, for example cancellous bone material.

References herein to the orientation of an apparatus, such as top, bottom, lower and upper, will refer to the apparatus in an access orientation.

Figure 1:
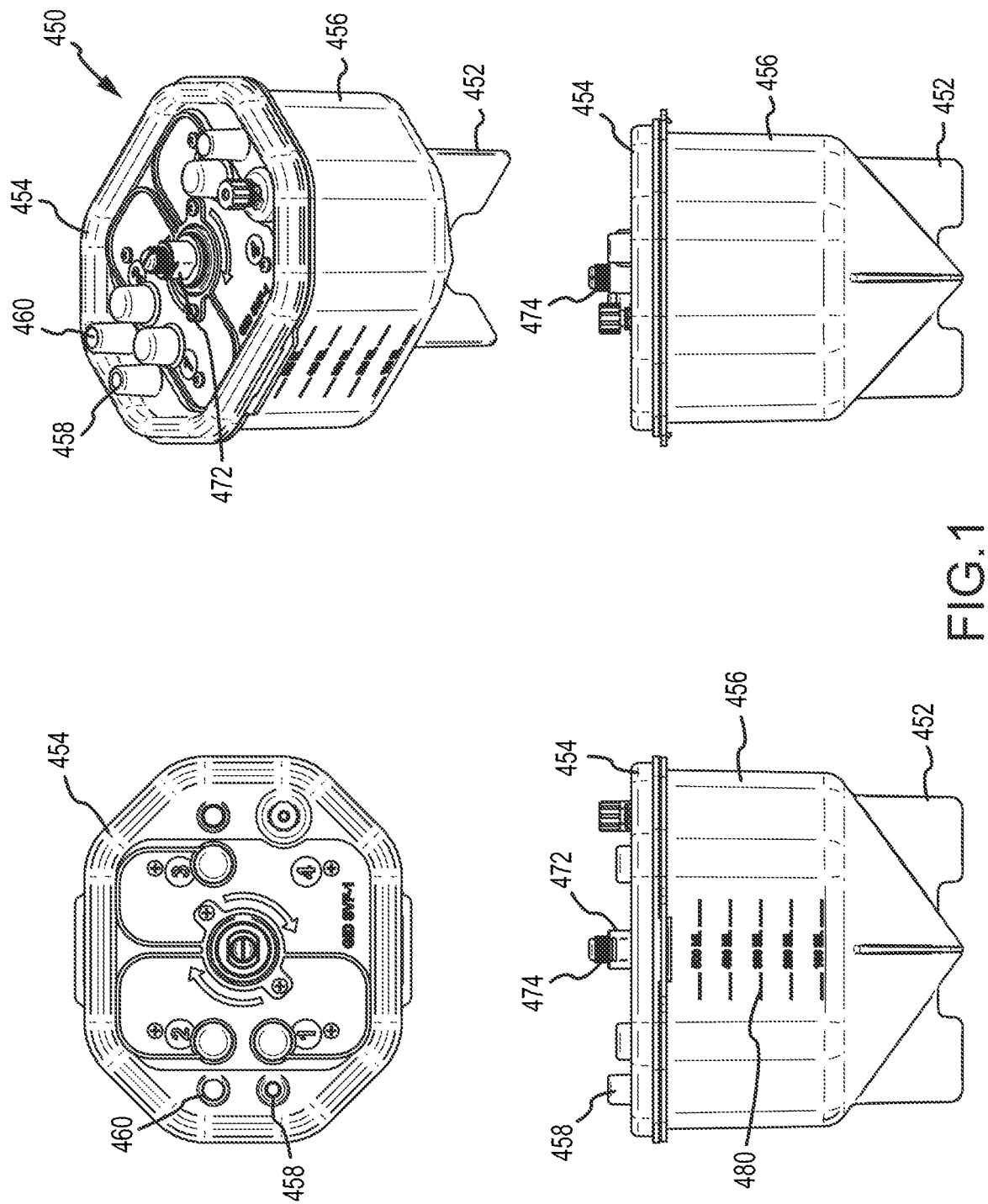
FIG. 1 shows top, perspective, side and end views of another embodiment of a tissue collection and processing apparatus.
Figure 2:
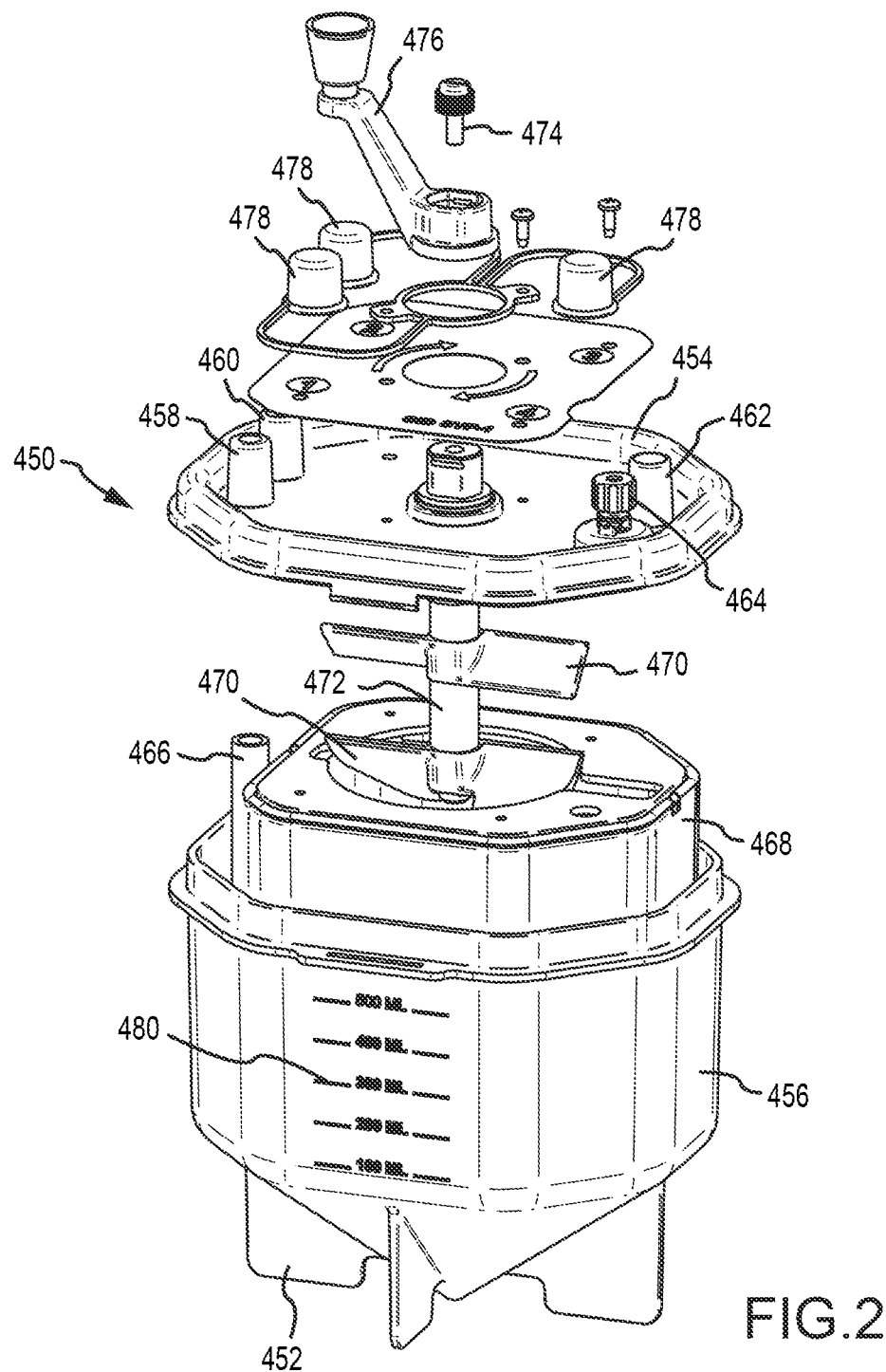
FIG. 2 shows an exploded view of the same tissue collection and processing apparatus as FIG. 1.

Referring now to FIGS. 1 and 2, an embodiment is shown for a tissue collection and processing apparatus. As shown in FIGS. 1 and 2, a tissue collection and processing apparatus 450 has a collection orientation, also referred to herein as an access orientation, in a freestanding, upright position as supported by base supports 452. The apparatus 450 includes a lid 454 covering a bowl-like shell 456, which make up a container having an internal containment volume under the lid within the shell. The apparatus includes a first suction port 458, a second suction port 460, an inlet port 462 and an auxiliary access port 464.

The first suction port 458 is connected with a suction conduit 466 extending from the first suction port 458 to within a tapered portion of an internal containment volume of the apparatus 450. The second suction port 460 may be adapted to receive a translatable suction conduit for removal of material from a filtration volume, or downstream side, of a filter 468 to different elevations. The second suction port 460 may also provide an opening through which air may be drawn into the internal containment volume of the apparatus when material is being suctioned from the internal containment volume through the first suction port 458 and/or to permit expulsion of an when feed tissue is introduced into the inlet port 462. The filter 468 suspended from the lid 454 and the filter 468 divides the internal containment volume in the apparatus between a tissue retention volume disposed inside the filter 468 and a filtrate volume disposed on the other side of the filter 468. The apparatus 450 includes a rotatable mixer disposed within the filtrate volume that includes propellers 470 connected to a rotatable shaft 472, which may be rotated to operate the rotatable mixer and cause the impellers 470 to mix and circulate fluid within the internal containment volume of the apparatus 450. The rotatable shaft 472 includes an internal lumen that extends from a proximal end outside of the container of the apparatus to a distal end in the tissue retention volume, to permit access into the internal containment volume. A removable plug 474 may be disposed in a proximal end of the lumen for sealing the lumen when the lumen is not in use. The rotatable shaft includes a handle interface which may be interfaced with a hand-manipulable handle 476 (FIG. 2) to operate the rotatable mixer. The apparatus 450 includes attached caps 478 which may be used to cap the first suction portion 458, second suction port 460 and inlet port 462 as needed, such as to seal the container for transportation between processing locations or during agitation on a warmer-shaker during digestion operations. The apparatus 450 includes volume gradation markings 480 that indicate the volume contained within the tissue retention volume (within the filter 468) up to different elevations of the container 450 when in the access orientation.

Figure 3:
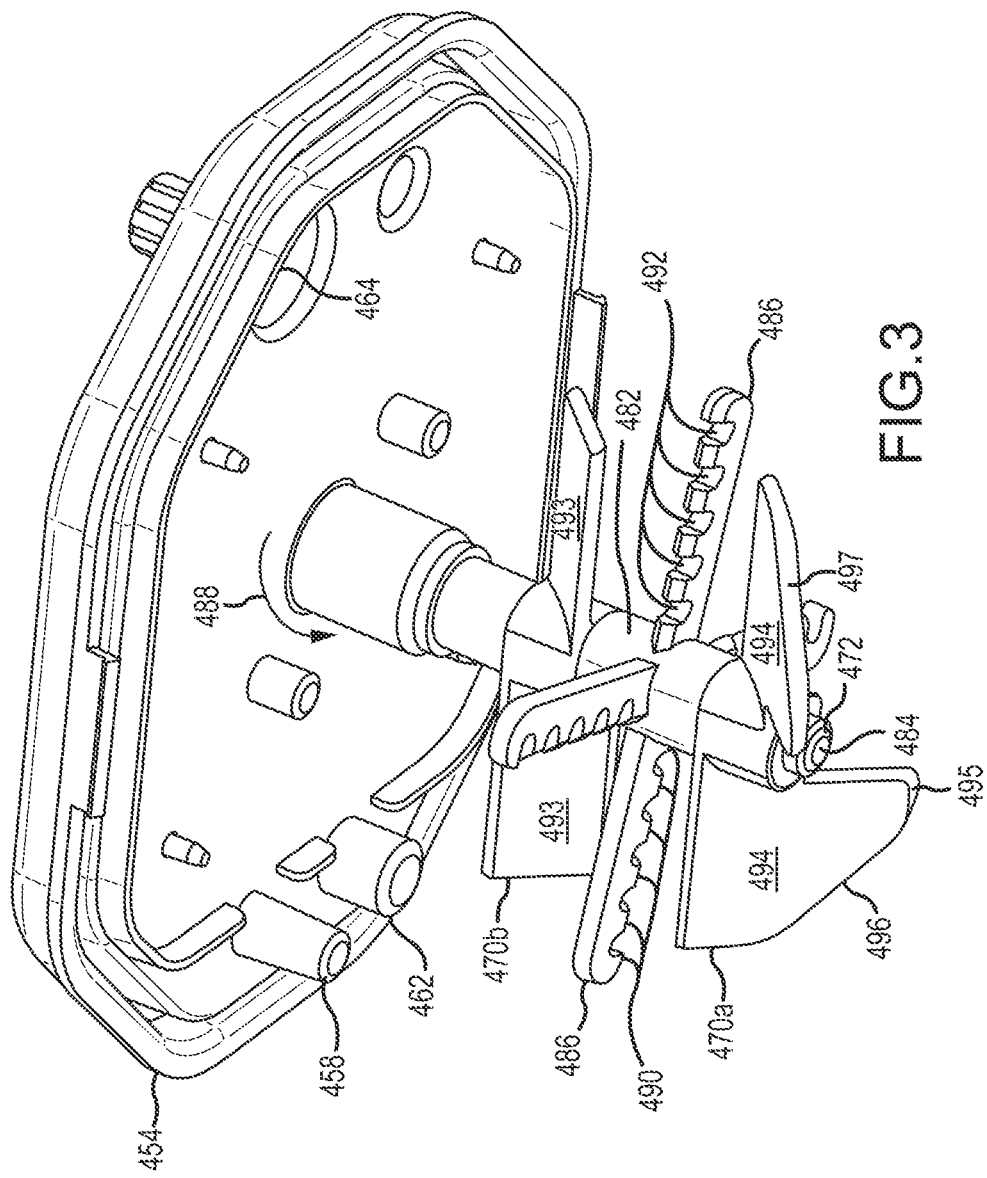
FIGS. 3 and 4 illustrate a portion of another embodiment of a tissue collection and processing apparatus including a rotatable tissue collector.
Figure 4:
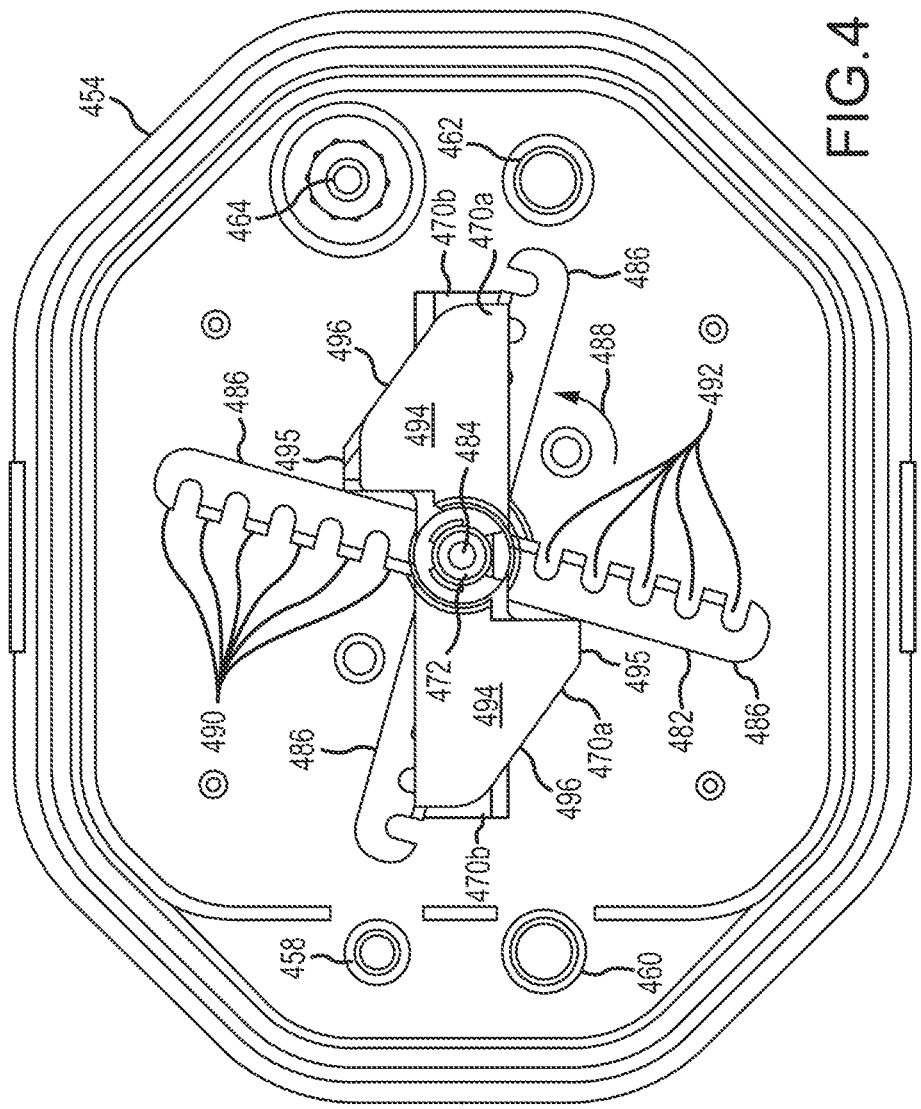
Figure 5:
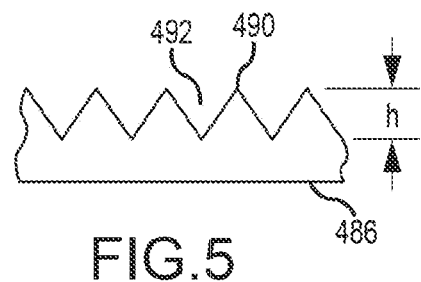
FIG. 5 illustrates an example tooth configuration for a toothed member for a rotatable tissue collector.
Figure 15:
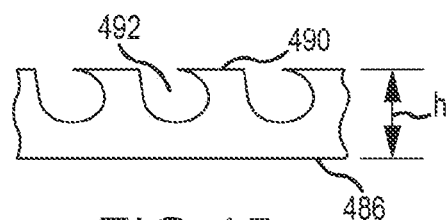
FIG. 15 illustrates another example tooth configuration for a toothed member for a rotatable tissue collector.
Figure 16:
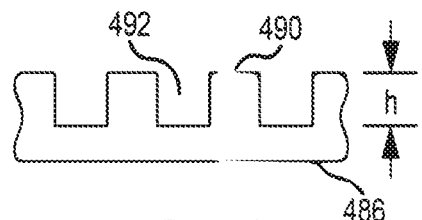
FIG. 16 illustrates another example tooth configuration for a toothed member for a rotatable tissue collector.

Reference is now made to FIGS. 1-4. FIGS. 1 and 2 show a tissue processing apparatus 450 with an example rotatable assembly. FIGS. 3 and 4 show a configuration for an alternative rotatable assembly that may be disposed in the tissue retention volume of a tissue collection and processing apparatus, and for convenience of description and brevity will be discussed in the context of an alternative embodiment of the apparatus 450 shown in FIGS. 1 and 2. The rotatable assembly shown in FIGS. 3-4 may be particularly advantageous for processing human biological material containing significant stringy tissue such as adipose tissue. Reference numerals used in FIGS. 3 and 4 are the same as used in FIGS. 1 and 2 for like features. FIGS. 3 and 4 show a rotatable tissue collector 482, which may alternatively be referred to as a tissue comb or more particularly as a stringy-tissue comb. As shown in FIGS. 3 and 4, the lid 454 has the first suction port 458, second suction port 460, inlet port 462 and auxiliary axis port 464 providing access through the lid 454 into the internal containment volume of the container of the apparatus 450. The mixing propellers 470 are shown mounted on the rotatable shaft 472. For convenience of description, in FIGS. 3 and 4 the lower propeller is designated 470a and the upper propeller is designated 470b. Also shown is a terminal end of a lumen 484 that passes through the rotatable shaft 472 to provide access from above the lid 454 into the internal containment volume of the container of the apparatus 450. The term mixing propeller is used interchangeably herein with the term mixing impeller.

As shown in FIGS. 3 and 4, the tissue collector 482 is disposed on the shaft 472 intermediate between the propeller 470a and propeller 470b. The propellers 470 may alternatively be referred to as impellers or mixing impellers. Also shown in FIGS. 3 and 4 is a rotational direction 488 represented by an arrow and showing a rotational direction for rotating the shaft 472 to rotate the propellers 470 and the tissue collector 482 during one possible operation of the apparatus. The rotational direction 488 corresponds with the directional arrows on a plate shown in FIG. 2 that is visible at the top of the device to show direction of rotation for operation of the apparatus 450.

The tissue collector 482 includes four tissue collection members 486, which may also be referred to as tissue collection blades. The tissue collection members 486 each includes a plurality of teeth 490 and open spaces 492, configured with an open space 492 located between each pair of adjacent teeth 490. The tissue collection members 486 thus have a toothed configuration that facilitates engagement and collection of stringy tissue, such as collagen, when the tissue collector 482 is rotated in the rotation direction 488, such as may be affected by rotating the rotatable shaft 472 using the handle 476. The open spaces 492 may alternatively be referred to as slots or recesses, and the open spaces 492 provide locations for stringy tissue engaging with the tissue collector 482 to be collected and retained, when material being processed includes stringy tissue. As stringy tissue collects in the open spaces 492, the stringy tissue may also tend to wrap around the rotatable shaft 472 to assist retention of the stringy tissue. By collecting and retaining the stringy tissue using the tissue collector 482, plugging of the filter 468 may be significantly reduced because less of the stringy tissue is available to collect on and plug the filter 468. The teeth 490 each have a top (maximum protrusion of a tooth 490 relative to the bottom of an adjacent open space 492) that is thus disposed toward a leading edge of the corresponding member 486 when the tissue collector 482 is rotated in the rotational direction 488. The bottom of an open space 492 may be the most recessed portion of the open space relative to the top of an adjacent tooth 490 as defined by the surface geometry of the member 486. In the configuration shown in FIGS. 3 and 4, each member 486 includes six teeth 490 and five open spaces 492.

With continued reference to FIGS. 1-4, features of one or both of the propellers 470 may be configured to assist collection of stringy tissue by the tissue collector 482 and to reduce potential for plugging of the filter 468. As shown in FIGS. 1-4, one or both of the propellers 470 may have pitched blades that direct flow of fluid from the respective propeller 470 in an axial direction relative to the axis of rotation of the rotatable shaft 472. As shown in FIGS. 3 and 4, the configuration of the bottom propeller 470*a* may include impeller blades 494 that are pitched at an angle that will propel fluid flow in an upper axial direction along the rotatable shaft 472 directed toward the tissue collector 482 when the rotatable shaft 472 is rotated in the rotational direction 488. This type of upward pumping action by the propeller 470*a* may assist in moving stringy tissue away from the filter 468 and toward the tissue collector 482 to engage and collect on the members 486. In similar manner, as shown in FIGS. 3 and 4, the top propeller 470*b* may have pitched blades 493 that propel fluid flow in an axial direction upward toward the underside of the lid 454 and away from the tissue collector 482 when the rotatable shaft 472 is rotated in the rotational direction 488. This upward pumping action by the propeller 470*b* may assist in pulling tissue through the tissue collector 482 to promote collection of stringy tissue by the members 486. As a design enhancement, the tissue collection members 486 may extend in a radial direction outward from the axis of the rotatable shaft 472 to a greater distance than either one of or both of the blades of the propellers 470*a,b*. In particular, it is preferred that the members 486 may extend in a radial direction a distance that is beyond the radial distance of a maximum extent of the blades 494 of the bottom propeller 470*a*, and in a further enhancement the members 486 may extend in a radial direction farther than a maximum extent of the blades 493, 494 of either of the propellers 470*a* and 470*b*. In this way the members 486 may be configured to collect stringy tissue beyond the radial extent of one or both of the propellers 470*a,b*.

In one enhancement, one or more of the blades 494 may be configured to scrape at least a portion of the filter 468 when the rotatable shaft 472, and thus also the bottom propeller 470*a*, is rotated in the rotational direction 488. In the configuration shown in FIGS. 1-4, such scraping of the filter 468 may be accomplished by configuring a bottom edge portion 495 and/or slanted edge portion 496 of a blade 494 to contact and scrape surfaces of the filter 468. In that regard, the slanted edge portion 496 of a blade 494 may be configured to correspond with and contact a corresponding tapered portion of the filter 468. A leading edge of the blade 494 may have a tapering width to assist in scraping tissue away from the surface of the filter 468. For example, the configuration of the blade 494 as shown in FIG. 3 includes a beveled surface 497 toward a leading edge of the slanted edge portion 496 that may help to lift tissue away from the filter 468 when the lower propeller 470*a* is rotated in the rotational direction 488.

As shown in FIGS. 3 and 4, the teeth 490 of the members 486 may have beveled surfaces toward a leading edge that facilitate easier rotation of the tissue collector 482 through tissue that may be disposed in the tissue retention volume of the container of the apparatus 450.

A rotatable tissue collector, for example as shown in FIGS. 3 and 4, may preferably be used in combination with at least one mixing impeller and/or in combination with at least two mixing impellers (as shown in example of FIGS. 3 and 4). Alternatively, the tissue collector may be used by itself and not in combination with any separate mixing impeller. When a separate mixing impeller is used, one or more such separate mixing impeller may include one or more pitched blades (e.g., blades 494, 493 of propellers 470*a,b* of FIGS. 3 and 4) that impart axial flow for mixing, or one or more such separate mixing impeller may include one or more unpitched blades that impart radial flow. When a rotatable tissue collector is used alone, without any separate mixing impeller, the tissue collector by itself may serve also as a rotatable mixer with the tissue collection members also acting as mixing members to mix contents within a tissue retention volume. In a preferred implementation when processing adipose tissue, a rotatable tissue collector is used in combination with at least one mixing impeller. When only one mixing impeller is present, it is more preferred to dispose the mixing impeller at a lower elevation on a rotatable shaft (e.g., propeller 470*a* of FIGS. 3 and 4) although an alternative arrangement is to include the mixing impeller at a higher elevation on a rotatable shaft (e.g., propeller 470*b* of FIGS. 3 and 4). A preferred configuration is for each mixing impeller and tissue collector to be coaxial and connected to and rotatably driven by a single rotatable shaft, although such a single shaft arrangement is not required. For instance, one or more mixing impellers may be connected to and driven by one or more rotatable shafts separate from a rotatable shaft that drives a rotatable tissue collector. A tissue collection and processing apparatus may have multiple rotatable tissue collectors, which may have the same or different configurations and may be driven by the same or different rotatable shafts.

The teeth and adjacent open spaces on tissue collection members of a rotatable tissue collector may have a variety of configurations. It is not necessary that the teeth be of the same height or configuration or that the open spaces be of the same size or configuration, either on the same tissue collection member or on different tissue collection members.

Figure 17:
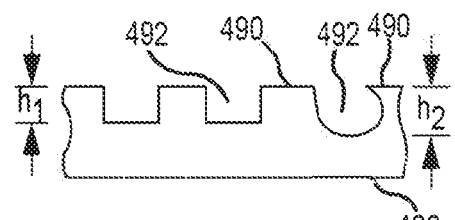
FIG. 17 illustrates another example tooth configuration for a toothed member for a rotatable tissue collector.
Figure 18:
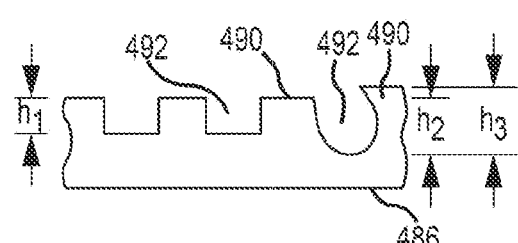
FIG. 18 illustrates another example tooth configuration for a toothed member for a rotatable tissue collector.

Reference is made to FIGS. 5 and 15-18 showing some example configurations for open spaces and teeth for a tissue collection member. Reference numerals corresponding with the tissue collection members, teeth and open spaces are the same as used in FIGS. 3 and 4, for convenience of description. FIGS. 5 and 15-18 show five example configurations showing some examples for different configurations for teeth 490 and open spaces 492 for a tissue collection member 486. Examples in FIGS. 5, 15 and 16 all have teeth 490 that have a height h (distance between the top of a tooth 490 and the bottom of an adjacent open space 492) that is equal for all teeth 490. The example in FIG. 17 shows a configuration in which some teeth 490 have a greater height $h_2$ than the height $h_1$ of some other teeth 490. The example in FIG. 18 shows a configuration with three different tooth heights ($h_1$, $h_2$, $h_3$). The examples in FIGS. 16 and 17 also show configurations in which not all of the teeth 490 and the open spaces 492 are configured with the same geometry.

Figure 6:
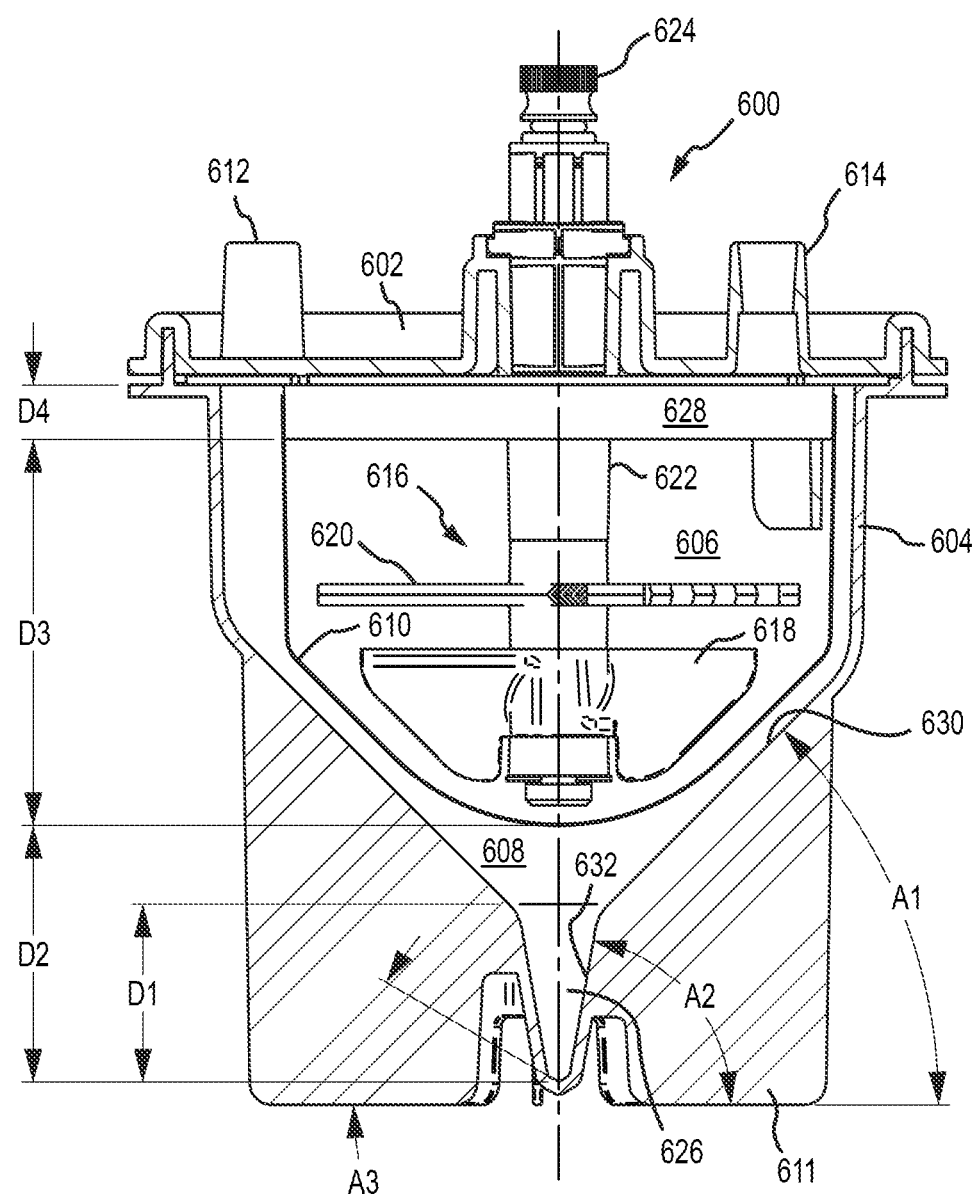
FIG. 6 shows a sectional view illustrating some features of another embodiment of a tissue collection and processing apparatus.

Reference is made to FIG. 6, which shows another embodiment for a tissue collection and processing apparatus. FIG. 6 shows an apparatus 600 including a lid 602 and a shell 604 that form a container having an internal containment volume including a tissue retention volume 606 and a filtrate volume 608 disposed on different sides of a filter 610. The apparatus 600 is shown in an access orientation as it would be supported by base supports 611 that are integrally formed with the shell 604. A suction port 612 is in fluid communication with the filtrate volume 608 and through which material may be removed from the filtrate volume 608. An inlet port 614 is provided for introducing tissue or other material into the tissue retention volume 606. The apparatus 600 may include additional access ports (e.g., additional suction port, auxiliary port), such as described for previous embodiments. The apparatus 600 includes a rotatable assembly 616 including a mixing impeller 618 and a tissue collector 620. The mixing impeller 618, tissue collector 620 and a spacer 622 are mounted on a rotatable shaft (not shown) that extends from above the container through the lid 602 and into the tissue retention volume 606. The rotatable shaft includes a central lumen that extends through the rotatable shaft from outside the container and opens at the bottom of the mixing assembly near the bottom portion of the tissue retention volume 606 just above the filter 610. The lumen is accessible by removing a cap 624. The lid 602, shell 604, tissue retention volume 606, filtrate volume 608, filter 610, base supports 611, suction port 612, inlet port 614, rotatable shaft, mixing impeller 618 and tissue collector 620 may have any design features or configurations as described previously in relation to corresponding features of the apparatus described in any of FIGS. 1-5. The apparatus 600 does, however, include a pellet well 626 at the bottom of the filtrate volume 608, as discussed further below. Such a pellet well design could also be incorporated into apparatus illustrated in FIGS. 1-4.

In some preferred implementations, the tissue collector 620 may have a design similar to the corresponding tissue collector described with respect to FIGS. 3-4 and the mixing impeller 618 may be configured with pitched blades for producing axially upward flow toward the tissue collector 620 when the rotatable shaft is rotated in an appropriate direction. The blades of the mixing impeller 618 may beneficially be designed with portions that scrape the filter 610 as the rotatable shaft 616 is rotated, in a manner similar as described above with respect to FIGS. 1-4. The lumen through the rotating shaft may be aligned with a collection volume located in the filtrate volume 608 below the bottom of the filter 610, and may provide access for convenient removal of processed material from the pellet well 626 in the collection volume located below the filter 610.

Various example dimensions are shown for the apparatus 600. A first height dimension $D_1$ shows the vertical dimension from the bottom of the collection volume at a nadir of the filtrate volume 608 to a top elevation of the collection volume occupied by the pellet well 626. Second height dimension $D_2$ shows the vertical dimension from the bottom to the top of the collection volume that is below the filter 610. Third height dimension $D_3$ shows the vertical dimension from the bottom of the filter 610 to the bottom of a skirt 628 from which the filter 610 is suspended. Fourth height dimension $D_4$ shows the vertical extent of the skirt 628. Angle $A_1$ is an angle between horizontal and a first tapered interior wall surface 630 of the container that defines at least a portion of the filtrate volume 608, including defining at least a portion of the collection volume. Angle $A_2$ is an angle from horizontal to a second tapered interior wall surface 632 of the container that defines at least a portion of the pellet well. Angle $A_3$ is an angle between horizontal and a third tapered interior wall surface of the container that defines at least a bottom portion of the pellet well 626. Example dimensions for one example implementation for the embodiment of the apparatus 600 includes 25.7 millimeters for $D_1$, 37.1 millimeters for $D_2$, 55.9 millimeters for $D_3$, 7.9 millimeters $D_4$, 45° for $A_1$, 80° for $A_2$, and 300 for $A_3$. Such an example may be designed for example to include an internal containment volume of about 270 cubic centimeters and a volume in the pellet well 626 of about 1.2 cubic centimeters, and with the filtrate volume 606 configured to accommodate processing of about 110 cubic centimeters of adipose tissue in the tissue retention volume 606 for preparation of a pellet phase including leuko stromal vascular fraction concentrate that may fill or nearly fill the pellet well 626.

Figure 7:
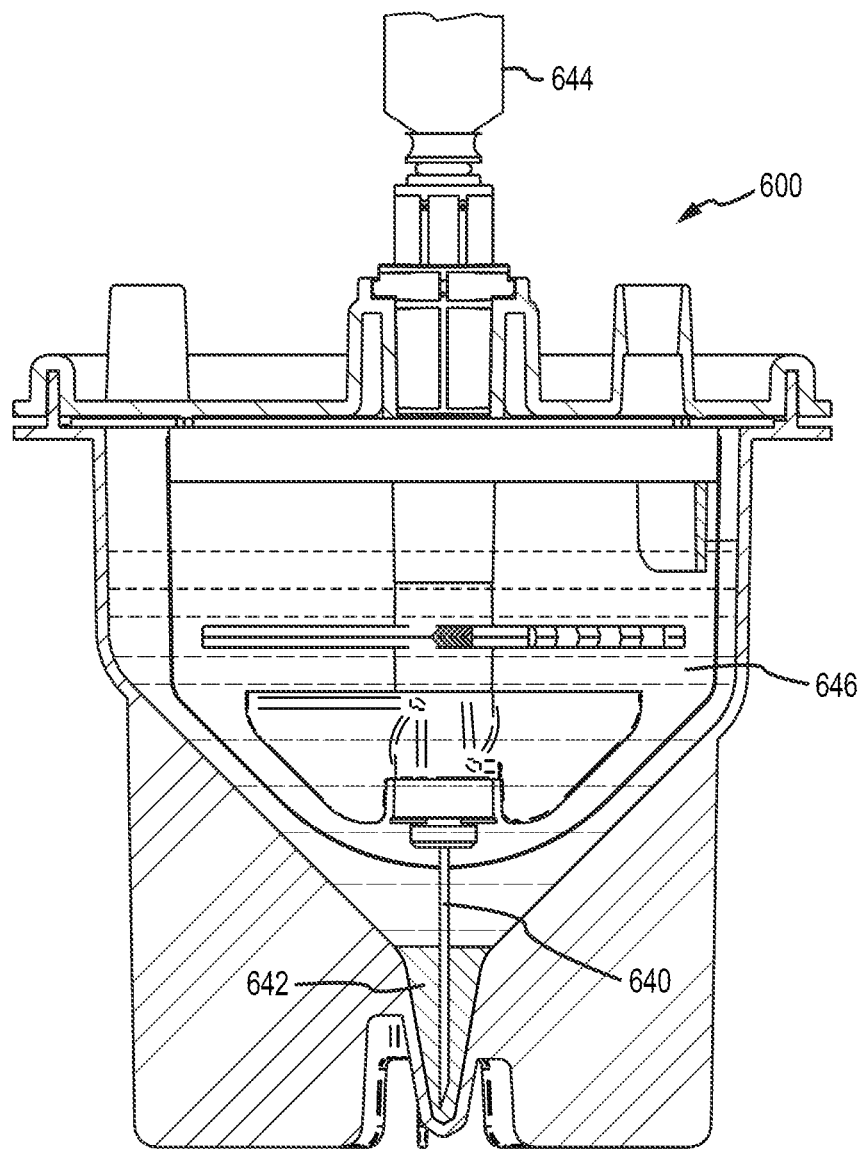
FIG. 7 illustrates the same tissue collection and processing apparatus as FIG. 6 showing a needle inserted into a pellet well to aspirate pellet phase material.

The location and configuration of the pellet well 626 in the embodiment of the apparatus 600 shown in FIG. 6 facilitates direct aspiration of material of a pellet phase that may collect in the pellet well 626 by providing a relatively deep and narrow chamber that helps facilitate effective aspiration of the pellet phase material without also aspirating large quantities of overlying material from less-dense material phases that may form during centrifuge processing. FIG. 7 shows the apparatus 600 of FIG. 6 in which a hypodermic needle 640 is inserted through the lumen of the rotatable shaft to access pellet phase material 642 from above for direct aspiration of the pellet phase material 642 from the pellet well 626 through the hypodermic needle 640 to outside of the container and into a syringe 644. Such direct aspiration of the pellet phase material 642 may be performed without first removing less-dense material 646 from above the pellet phase material 642 and without suspension of the pellet phase material 646 in a suspension liquid. The syringe 644 may be preloaded with a quantity of dispersion medium that mixes with and disperses aspirated pellet phase material as it is introduced into the syringe 644. This may help prevent clumping of the pellet phase material in the syringe. The resulting mixture of pellet phase material and dispersion medium may be removed and further processed to prepare a composition for administration to a patient or the mixture may be directly administered to a patient as a delivery composition, such by injection into a patient in the vicinity of a joint to treat for osteoarthritis at the joint. If a mixture in the syringe is removed from the syringe 644 for further processing, the mixture may be centrifuged to separate pellet phase material and suspension liquid and the separated pellet phase material may be recovered and formulated with other components in a delivery composition, which may for example include a scaffold material or may include dispersion in a new dispersion medium with properties and at a volume desired for a particular treatment application. Any of the wall surfaces defining at least a portion of any of the first tapered portion, second tapered portion and third tapered portion may have inclined planar geometry with a constant angle of inclination, as shown in FIGS. 6 and 7 for angles $A_1$, $A_2$ and $A_3$ or may have a curved geometry with a changing angle of inclination. When such a surface has a curved geometry, the respective angle, may be the angle of inclination of a line tangent to a point on the curved geometry.

Figure 10:
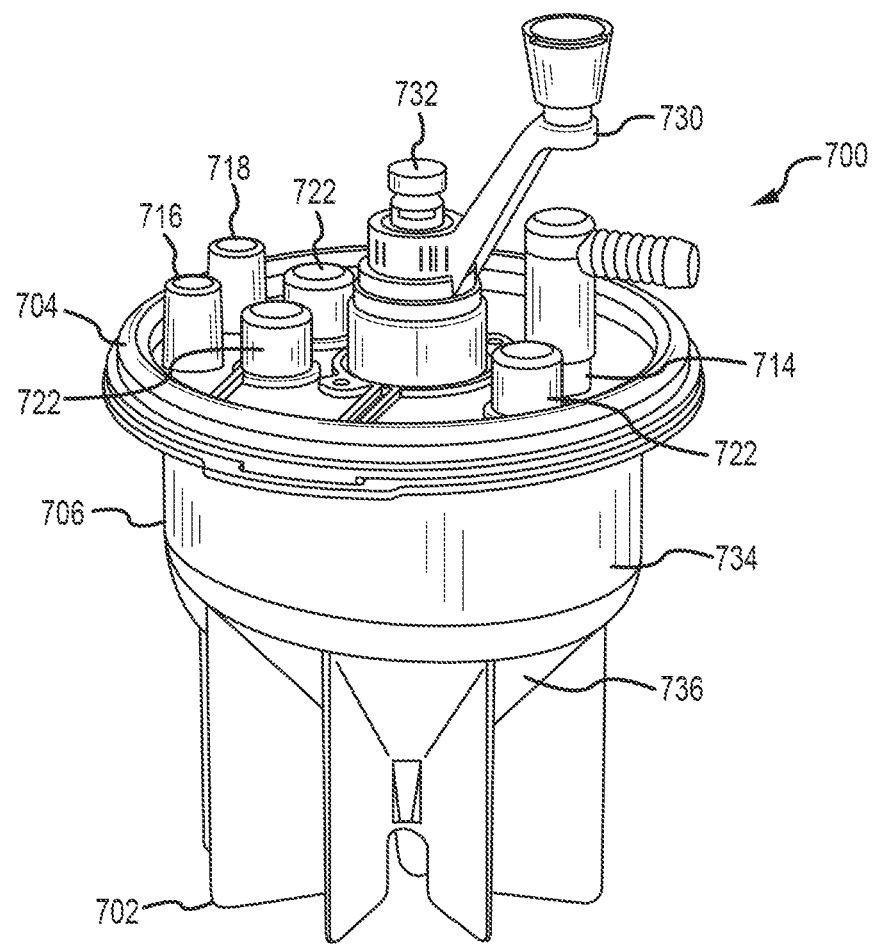
FIG. 10 is a perspective view of illustrates another embodiment of a portable container apparatus.
Figure 11:
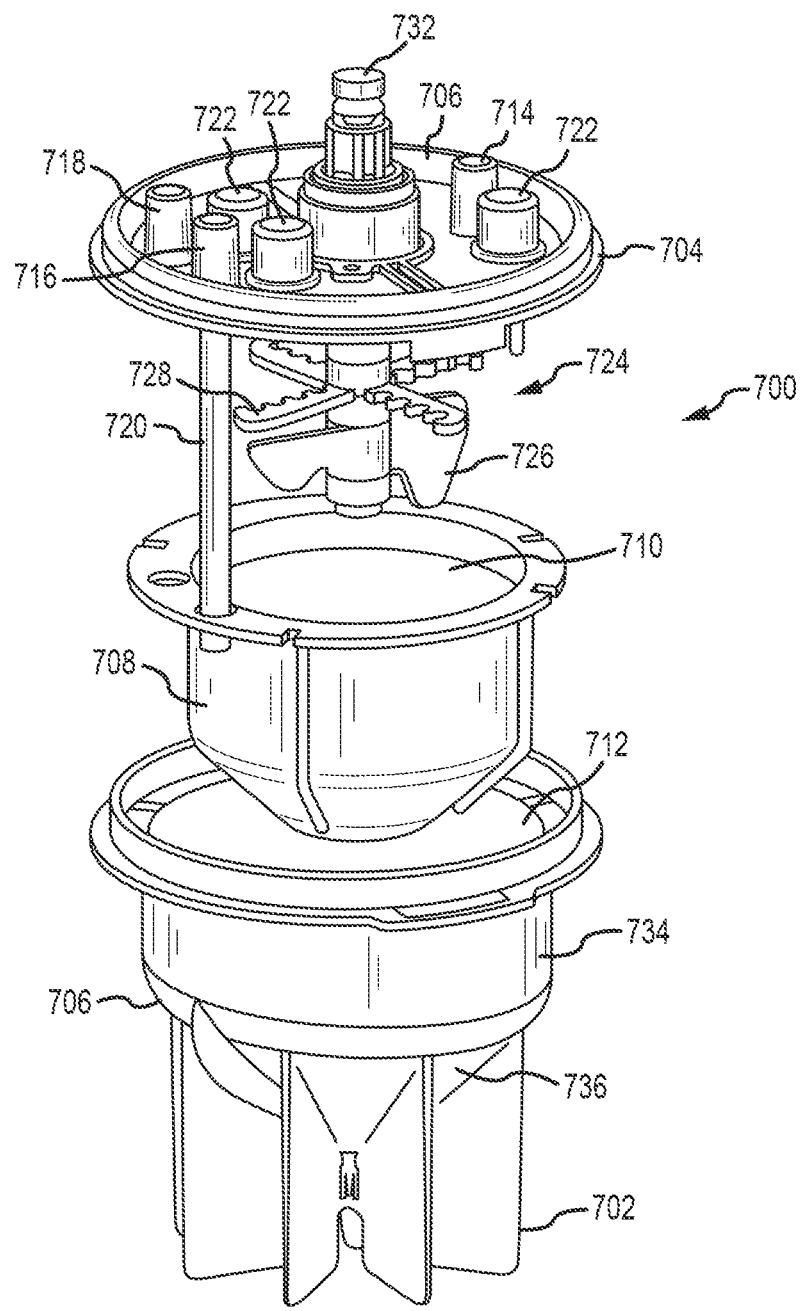
FIG. 11 is an exploded view of the portable container apparatus of FIG. 10.

FIGS. 10 and 11 show another embodiment for a portable container apparatus. In FIGS. 10 and 11, a portable container apparatus 700 is shown in an access orientation in a free-standing, upright position as supported by base supports 702. The apparatus 700 includes a lid 704 and a bowl-like shell 706, which together make up a container having an internal containment volume within the container. A filter 708 divides the internal containment volume into a tissue retention volume 710 inside the filter 708 and a filtrate volume 712 disposed on the other side of the filter 708 between the filter 708 and the shell 706. An inlet port 714 provides access to the tissue retention volume, for example to introduce adipose tissue into the tissue retention volume for processing. A first suction port 716 and an additional port 718 (e.g., second suction port or vent port) provide access to the filtrate volume 712, for example to suction fluids from the filtrate volume 712. The first suction port 716 is connected with a suction conduit 720 extending from the first suction port 716 to within a tapered portion of the internal containment volume of the apparatus 700. The additional port 718 may be adapted to receive a translatable suction conduit. Caps 722 attached to the lid 706 may be used to cover the first suction port 716, additional port 718 and inlet port 714 as needed. The apparatus 700 includes a rotatable assembly 724 including a mixing impeller 726 and a tissue collector 728 mounted on a rotatable shaft. The rotatable shaft is rotatable by a hand-manipulable handle 730 (shown in FIG. 10). A lumen extends through the rotatable shaft to provide access from outside of the apparatus 700 into the internal containment volume of the apparatus. The apparatus 700 is shown fitted with a cap 732 that may be removed to permit access to the lumen through the rotatable shaft. The lid 704, shell 706, filter 708, tissue retention volume 710, filtrate volume 712, inlet port 714, first suction port 716, additional port 718, suction conduit 720, mixing impeller 726, tissue collector 728, rotatable assembly 724 and the rotatable shaft and lumen therethrough for the apparatus 700 may have any design feature or features or configurations described previously in relation to corresponding features of any apparatus described in any of FIGS. 1-7, except as specifically noted. As described previously for the tissue collector 620 of apparatus 600 shown in FIGS. 5, 15-18 and 6, the tissue collector 728 of apparatus 700 may help to collect stringy tissue components that may be present to inhibit plugging of the filter 708 by such stringy tissue components.

As distinguished from the apparatus embodiments shown in FIGS. 1-4, the apparatus 700 has a generally circular container cross-section, as opposed to the octagonal container cross-section for the apparatuses of FIGS. 1-4. The circular shape may be advantageous for providing a flexible design for processing a wide range of tissue volumes and for compatibility with a variety of common centrifuges.

Figure 12:
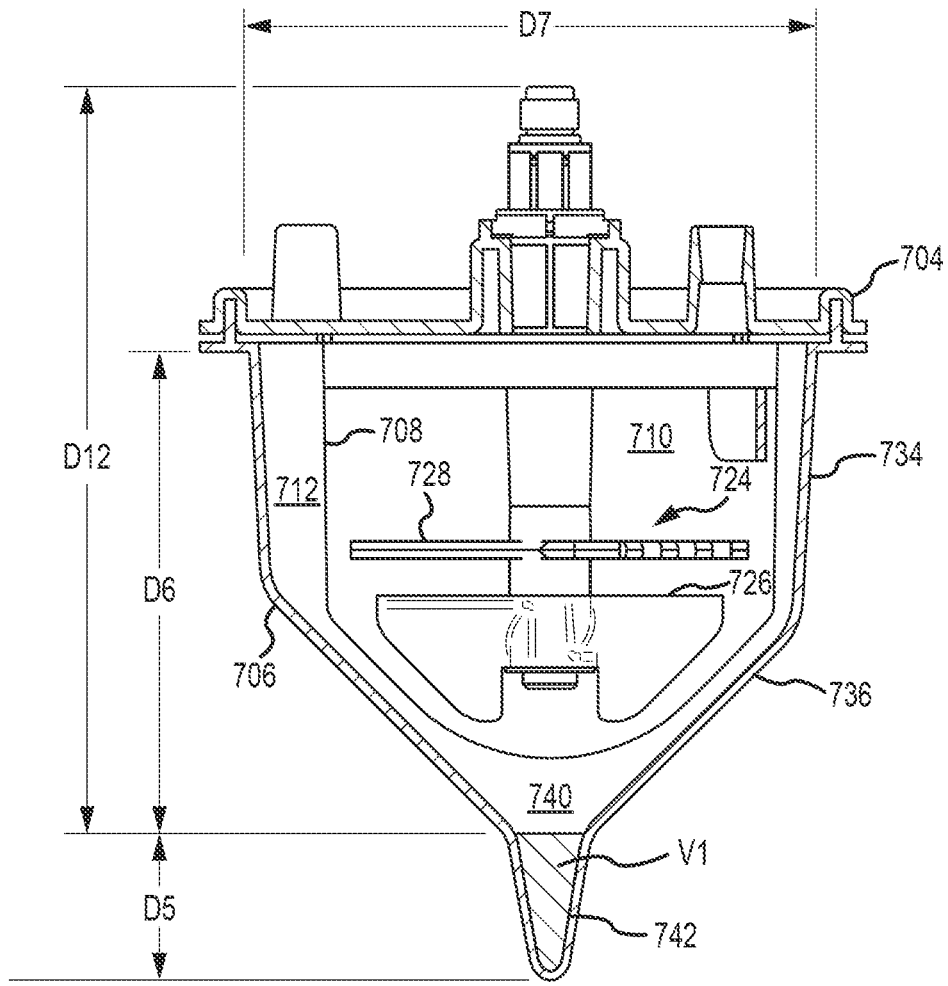
FIG. 12 is a sectional view of a container of the portable container apparatus of FIG. 10 illustrating features of the container.
Figure 13:
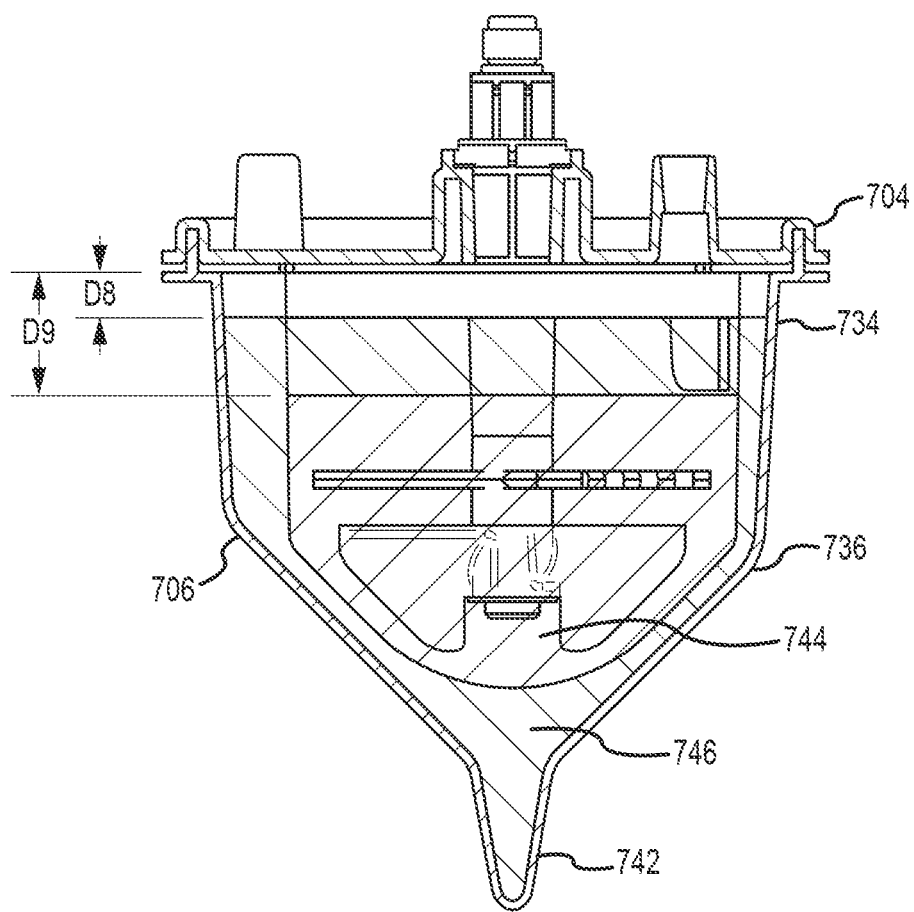
FIG. 13 is a sectional view of a container of the portable container apparatus of FIG. 10 illustrating an example of processing a relatively large volume of biological material in the container.
Figure 14:
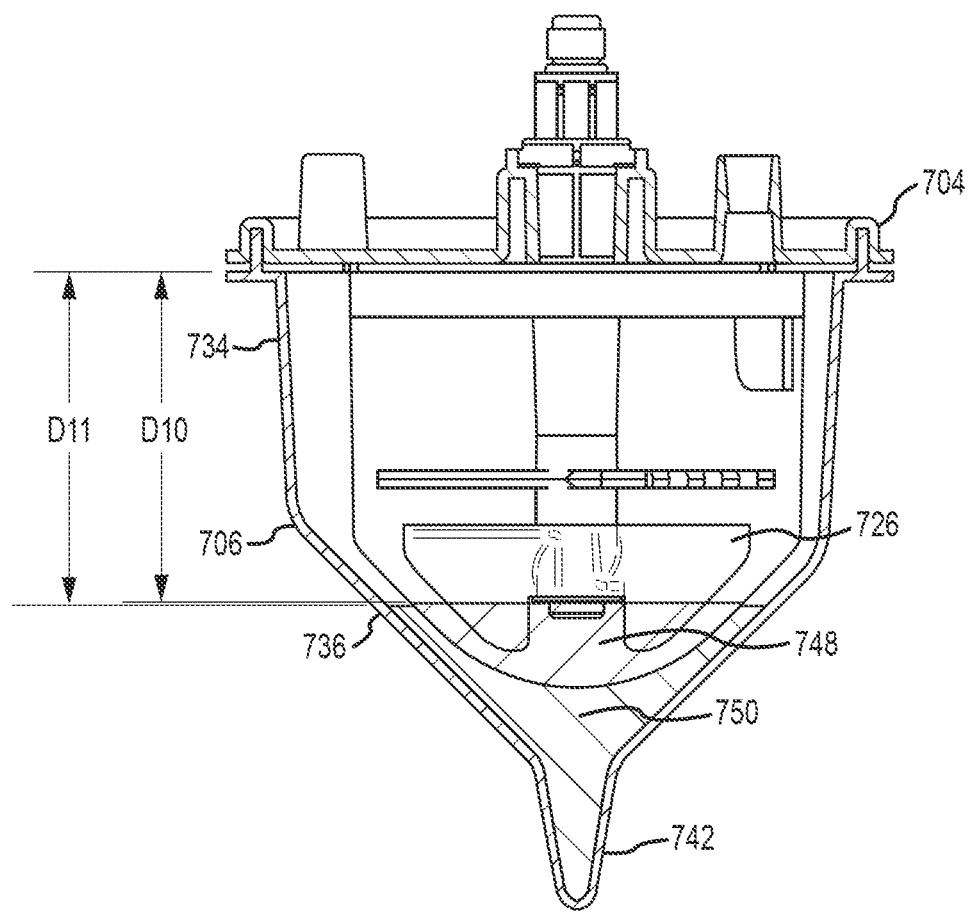
FIG. 14 is a sectional view of a container of the portable container apparatus of FIG. 10 illustrating and example of processing a relatively small volume of biological material in the container.

The shell 706, and the internal containment volume within the shell 706 and the lid 704, includes a first portion 734 and a second portion 736. The first portion 734 is a portion of the internal containment volume that has a substantially circular cross-section that either does not taper (e.g., is cylindrical) or that tapers only minimally. In that regard, the internal wall surface of the first portion 734 may be inclined relative to horizontal at an angle of from 70° to 90°. The second portion 736 includes a portion of the internal containment volume that tapers at a significant rate in a direction toward the bottom of the apparatus 700. The internal wall surface of the second portion 736 may preferably be inclined relative to horizontal at an angle in a range having a lower limit of 30°, 35°, 40°, 42° or 45° and an upper limit of 60°, 55°, 50°, 48 or 45°, with about 45° being preferred for some implementations. The second portion 736 may taper downward toward a pellet well configured to collect pellet phase material including stromal vascular fraction cells. The pellet well may include a third portion of the internal containment volume that does not taper in a downward direction or that tapers in a downward direction with an internal wall surface that may preferably be inclined relative to horizontal at an angle of from in a range being a lower limit of 70°, 75°, 80 or 85° and an upper limit of 90°. The first portion 734 may include a cylindrical shape or a frustoconical shape. The second portion 736 may each include a frustoconical shape. The third portion within the pellet well may include a cylindrical shape or a frustoconical shape. FIGS. 12-14 show an example implementation for the apparatus 700 including such a pellet well and designed for flexibility in processing a significant range of volumes of human biological material (e.g., collected adipose tissue).

FIG. 12 shows the lid 704 and the shell 706 of the apparatus 700 enclosing the filter 708 and the rotatable assembly 724 within an internal containment volume including the tissue retention volume 710 and the filtrate volume 712. The filtrate volume 712 includes a collection volume 740 located below a lowest elevation of the filter 708. Within the collection volume 740 is a pellet well 742 providing a volume V1 in which pellet phase material may collect during centrifuge processing of the apparatus 700 following enzymatic digestion.

FIGS. 13 and 14 illustrate flexibility of the apparatus 700 to process a wide range of human biological material volumes while providing sufficient processing volume to accommodate at least an equal volume of process liquid (e.g., wash liquid or digestion medium), FIG. 13 illustrates the internal containment volume of the apparatus 700 including a large volume of human biological material 744 disposed in the internal containment volume 710 and with an equal quantity of process liquid 746 (e.g., wash liquid or digestion medium) occupying the remaining portion of the available processing volume within the internal containment volume 710. FIG. 14 illustrates the internal containment volume of the apparatus 700 including a much smaller volume of human biological material 748 disposed within the tissue retention volume 710 along with an equal volume of process liquid 750. As shown in FIG. 14, the combined human biological material 748 and process liquid 750 fill a bottom portion of the available processing volume disposed within the second portion 736 to cover a lower tapered portion of the mixing impeller 726 for effective mixing. As will be appreciated, a smaller volume of human biological material could be effectively processed than shown in FIG. 14 by increasing the amount of process liquid relative to human biological material to achieve at least a similar filling of the available processing volume to cover a lower tapered portion of the mixing impeller. The volume ratio of process liquid to human biological material may be much larger than 1:1. For example, a small volume of human biological material (e.g., 5 or 10 cubic centimeters of adipose tissue) may be processed with at a volume ratio of digestion medium to human biological material in excess of 2:1 or at an even larger ratio.

The corresponding tapered features of the second portion 736 of the internal containment volume 736, the filter 708 and the mixing impeller 726 permit effective processing (e.g., washing or digesting) with mixing a very small volume of human biological material, while the volume provided by the first portion 734 of the internal containment volume permits flexibility to use the same apparatus to also effectively process with mixing a much larger volume of human biological material. The relatively deep and narrow profile of the pellet well 742 permits collection of a wide range of volumes of pellet phase material resulting from processing a wide range of human biological material volumes and permits effective removal of such a range of pellet phase material volumes from the pellet well 742, such as by direct aspiration from the pellet 742 well without dilution and without dispersing the pellet phase material in a suspension liquid.

FIGS. 12-14 show some dimensions in relation to for the apparatus 700. D5 is a height dimension to the top of the pellet well 742. D6 is a height dimension of the internal containment volume located above the pellet well. D7 is a maximum diameter of the circular cross-section of the outside of the shell 706 configured to be received in a centrifuge bucket, below a lip at the top of the shell 706 that would ordinarily be above the top of the centrifuge bucket during centrifuging. D8 is a distance below the lid 704 to the maximum fill level in the internal containment volume for the available processing volume of the apparatus 700. D9 is a distance below the lid 704 to which the tissue retention volume 710 may be filled with human biological material while still providing room for addition of process liquid in an amount of at least a 1:1 volume ratio of wash liquid to human biological material. D10 is a distance below the lid 704 showing a minimum design fill volume within tissue retention volume for desired mixing by the mixing impeller 726. D11 is a distance below the lid 704 showing fill volume of process liquid in the filtrate volume when the process liquid is present at a 1:1 volume ratio to human biological material corresponding with the fill level of human biological material shown in FIG. 14. D12 is a total height dimension of the apparatus 700 configured to be compatible with and not interfere with operation of a centrifuge in which the apparatus is to be received during centrifuging. Some example dimensions for one example design implementation for the apparatus 700 is for D5 of about 27 millimeters, D6 of about 85 millimeters, D7 of about 100 millimeters, D8 of about 8 millimeters, D9 of about 21 millimeters, D10 of 58 about millimeters, D11 of about 58 millimeters and D12 of about 150 millimeters, and with the internal wall surface of the shell 704 defining the second portion 736 being inclined at an angle of 45° relative to horizontal. Such a design may be configured with an available processing volume of about 350 cubic centimeters that accommodates processing a range of human biological material from a minimum of 20 cubic centimeters to a maximum of 175 cubic centimeters with adequate available processing volume to permit a volume ratio of human biological material to wash liquid (or to digestion medium) of at least 1:1. Such a design may include a volume V1 of the pellet well 742 for example of about 1.2 cubic centimeters. The pellet well 742 may for example have a maximum diameter (maximum horizontal cross-dimension for a circular cross-section) at the top of the pellet well of about 8 millimeters.

The apparatus embodiments illustrated in FIGS. 3-7 and 10-14 each includes a tissue collector (482 in FIGS. 3-4 at 620 in FIGS. 10-14). When processing adipose tissue, which contains significant stringy tissue, inclusion of a tissue collector is preferred, even if not required. When processing cancellous bone material, which does not contain stringy tissue, not including such a tissue collector is generally preferred to simplify the apparatus design, even though inclusion of a tissue collector is generally not detrimental to cancellous bone processing.

Figure 8:
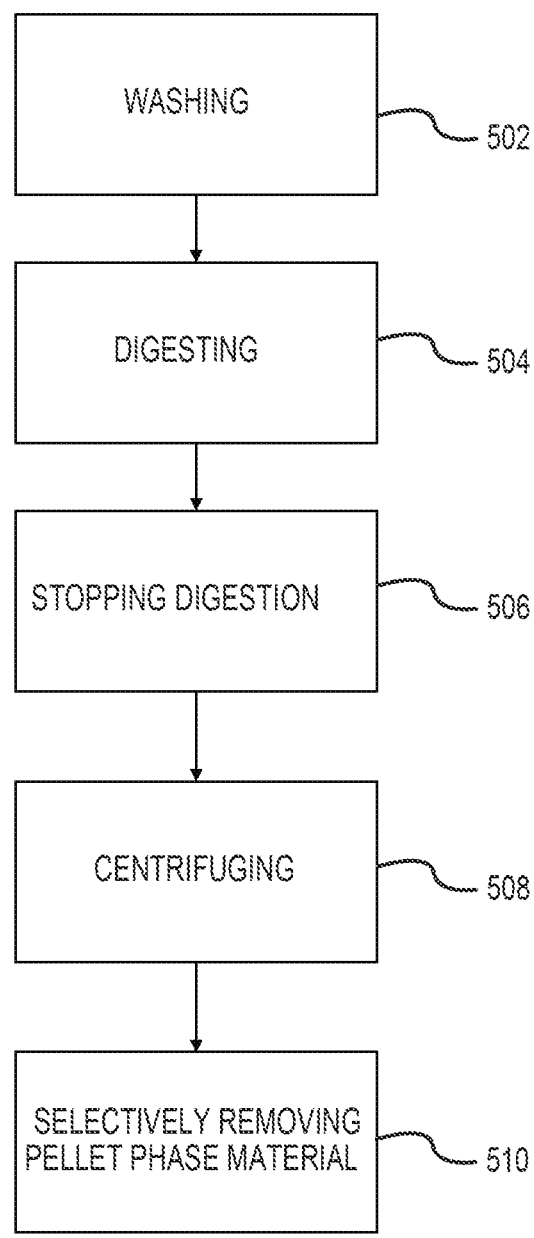
FIG. 8 is a generalized process block diagram of an embodiment of a method of processing adipose tissue.

FIG. 8 is a generalized process block diagram illustrating one embodiment of a method involving multi-step processing within a portable container, such as for example using a tissue collection and processing apparatus as previously described. As shown in FIG. 8, the method includes a washing step 502, during which adipose tissue disposed within a portable container is washed to remove contaminants from the adipose tissue. Contaminants that may be associated with the adipose tissue include for example blood, free lipids, small particles and debris and other materials that may have been collected with the adipose tissue or result from degradation during a tissue collection operations.

The washing 502 may include one or multiple wash cycles during which adipose tissue is washed with wash liquid within the container. The wash liquid, for example, may be a buffer solution, such as Lactated Ringer's solution or Hank's Balanced Solution, and may have additional additives, such as one or more of an anti-clotting agent, an antibiotic and an antifungal. An anti-clotting agent may beneficially prevent coagulation of blood that may be present, and may assist effective washing of blood from the adipose tissue. Antibiotics and antifungals may help protect against problems associated with inadvertent outside contamination of the adipose tissue within the container. Such a wash liquid may also include one or more additional buffering agents, such as glycine. One preferred material for use as an anti-clotting agent is heparin.

During a wash cycle, the wash liquid is mixed with the adipose tissue in the container and then preferably substantially all of the wash liquid with washed contaminants from the adipose tissue is removed from the container from a filtrate volume on a first side of a filter within the container while retaining the washed adipose tissue in a tissue retention volume of the container on a second side of the filter.

The washing may include any of the features discussed above.

After the washing 502, the washed adipose tissue in the container is subjected to a digesting step 504. Digestion medium, such as comprising a collagenase enzyme solution, is added to the container to contact the washed adipose tissue. The digestion medium may for example be added in a volume ratio of in a range of from 0.6:1 to 2:1 digestion medium: adipose tissue. The digestion medium may contain collagenase enzyme, for example in an amount to provide from 150 to 300 collagen digestion units (CDU) per milliliter of catalytic volume. Catalytic volume refers to the total volume of the digestion medium and adipose tissue within the container to which the digestion medium is added. After the digestion medium is added to the container, enzymatic digestion within the container is permitted to proceed for a retention time, for example, of from 20 minutes to 50 minutes while the container is disposed in a temperature controlled environment maintained within a temperature range preferably of from 32° C. to 38° C., and with at least occasional, and preferably substantially continuous, agitation of contents to the container. The digesting step 504 may include any or any combination of the feature refinements and additional features discussed above.

The method as shown in FIG. 8 also includes a stopping digestion step 506 occurring after the digesting step 504. The stopping digestion step 506 should preferably occur no earlier than the end of the retention time for the enzymatic digestion in the temperature controlled environment, but in any event should more preferably be performed within 50 minutes following adding the digestion medium to the container during the digesting step 504. The stopping digestion step 506 includes adding a stopping reagent to the container to positively stop enzymatic activity within the container. This is important, because if enzymatic activity is not discontinued, digestion within the container may proceed to an undesirable degree in which the enzyme may destroy the viability of a significant number of the leuko stromal vascular cells.

As shown in FIG. 8, the method includes, after the stopping digestion step 506, a centrifuging step 508. The centrifuging step 508 is performed with the container disposed in a centrifuge and the centrifuge is operated to centrifuge the container to form density-separated phases within the container. These density-separated phases include a higher-density pellet phase rich in leuko stromal vascular cells, which pellet phase may form adjacent a bottom of the container. The density-separated phases also include lower-density material phases. By lower-density, it is meant that the lower-density material phases have a lower-density than the pellet phase. When the container is oriented with the pellet adjacent a bottom of the container (e.g., in an access orientation for the container), the lower-density material phases will be disposed in the container above the pellet phase. The lower-density material phases may include, in order of decreasing density, an aqueous layer, a disaggregated adipose layer (containing remnants of disaggregated adipose tissue) and an oil layer. The pellet phase is enriched in, and may be mostly or even substantially entirely comprised of, leuko stromal vascular cells (e.g., stromal vascular fraction). On a side of the pellet phase opposite the lower-density material phases may be disposed a small red blood cell phase. Provided that washing of the adipose tissue is thorough during the washing step 502, this red blood cell phase may be extremely small, and in some case may be difficult to distinguish from a bottom portion of the pellet phase. The centrifuging step 508 may include any or any combination of the feature refinements and additional features discussed above.

As shown in FIG. 8, the stopping digestion step 506 is performed after the digesting step 504 and prior to the centrifuging step 508. Such sequencing is preferred, but not required. In one variation, the stopping digestion step 506 may be performed after the centrifuging 508. However, because enzymatic digestion would continue during the centrifuging, such a variation in the sequence is not preferred, to provide better control over the timing and extent of the enzymatic digestion.

After the centrifuging step 508 has been completed, the container may be removed from the centrifuge and subjected to a step 510 of selectively removing pellet phase material. The leuko stromal vascular cells, which include stem cells, contained in the pellet phase represent a valuable product. For effective use of these valuable leuko stromal vascular cells, it is generally necessary to remove the cells from the container. This has been a significant problem in the context of using multi-step portable containers for processing that is addressable with various implementations of the invention. During the step 510, material of the pellet phase is removed from the internal containment volume of the container to outside of the container separate from the less-dense material phases. The step 510 may include any of the features as discussed above. In some processing alternatives, the pellet phase material may be directly aspirated through an aspiration tube (e.g., hypodermic needle) inserted into the pellet phase from above and material of the pellet phase may be directly aspirated from the container through the aspiration tube, for example into a syringe or other fluid receptacle located outside of the container.

Figure 9:
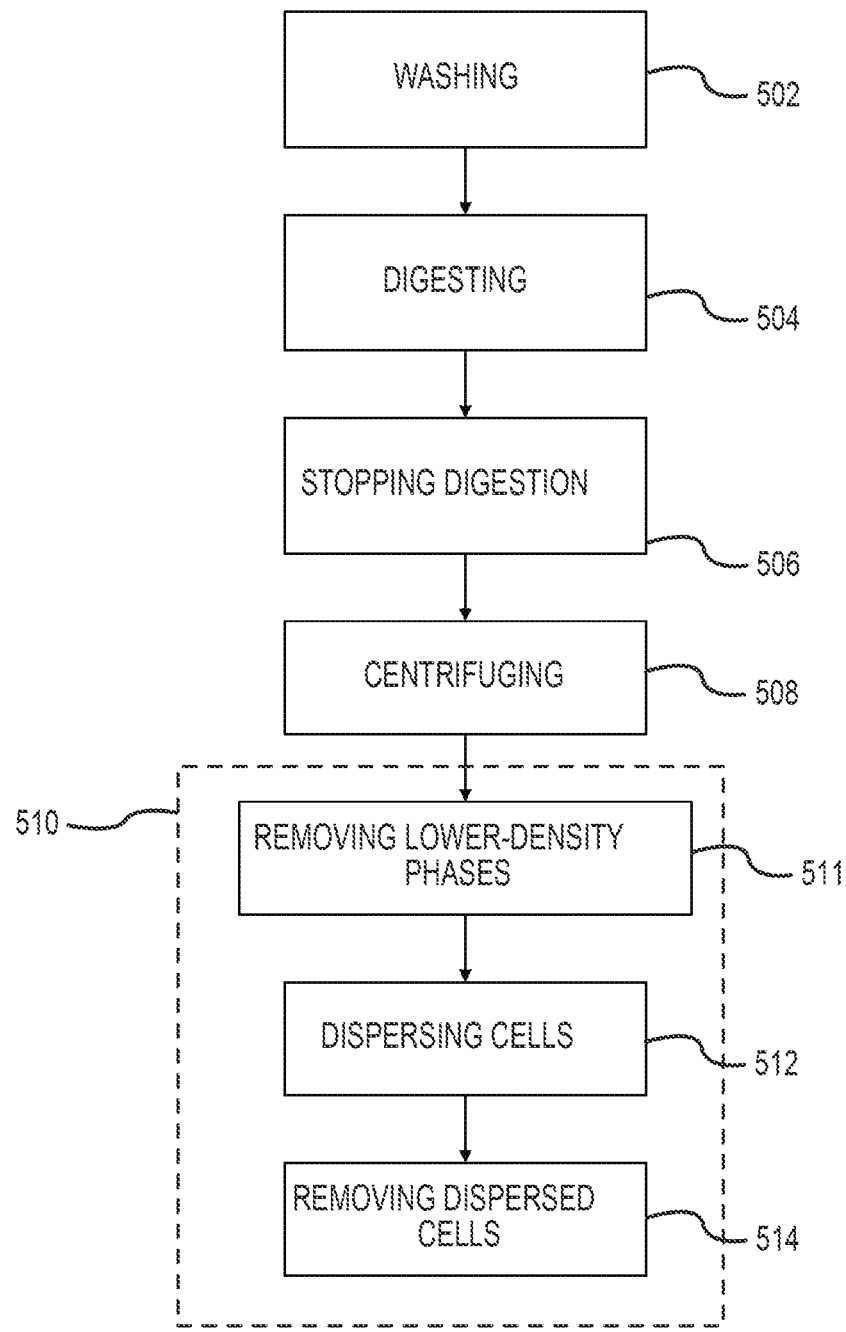
FIG. 9 is a generalized process block diagram of another embodiment of a method of processing adipose tissue.

Referring now to FIG. 9, another embodiment of implementation of a method is shown, including an alternative approach for selectively removing material of the pellet phase from the container that. The implementation shown in FIG. 9 includes the washing step 502, the digesting step 504, the stopping digestion step 506, the centrifuging step 508 and the selectively removing pellet phase material step 510 as discussed with FIG. 8, but showing more detail for some processing alternatives for step 510. As shown in FIG. 9, the step 510 includes steps 511, 512 and 514. During the step 511, the lower-density material phases formed during centrifuging may be removed from the container while the pellet phase is retained within the container, preferably while maintaining the pellet phase in an undisturbed state, in place at the location of the container where the pellet collected during the centrifuging. The step 511 may include any or any combination of the features as discussed above. As shown in FIG. 9, after the removing lower-density phases step 511, the method includes a dispersing cells step 512. During the dispersing cells step 512, aqueous suspension liquid is introduced into the container to mix with the pellet phase and to act as a dispersion medium for dispersing cells of the pellet phase in the suspension liquid. Dispersion of cells from the pellet phase may be aided by tapping the container to dislodge and break up the pellet phase to assist effective dispersion of the leuko stromal vascular cells in the suspension liquid. The dispersing cells step 512 may include any of the features as discussed above. After the dispersing cells step 512, the processing shown in FIG. 9 includes a removing dispersed cells step 514, during which most, and preferably substantially all, of the suspension liquid with the dispersed cells from the pellet phase is removed from the container, thereby recovering the leuko stromal vascular cell from the container. The removing dispersed cells step 514 may include any of the features discussed above.

As an alternative to the processing for the selectively removing pellet phase material step 510 shown in FIG. 9, after the removing lower-density material phases step 511, the material of the pellet phase could be removed from the container by direct aspiration through an aspiration tube, such as a hypodermic needle. With this processing alternative, the cells of the pellet phase material would not be dispersed or suspended in a suspension liquid prior to removal from the container.

Some example implementation combinations, which may be the subject of claims with or without additional features as disclosed above, are as follows:

1. An apparatus for processing human biological material containing stringy tissue, the apparatus comprising;
   a container having an internal containment volume, the internal containment volume including a tissue retention volume and a filtrate volume;
   a filter disposed within the internal containment volume with the tissue retention volume on one side of the filter and the filtrate volume on another side of the filter with the tissue retention volume and with the filtrate volume being in fluid communication through the filter;
   an inlet port in fluid communication with the tissue retention volume and configured to access the tissue retention volume for introducing human biological material into the tissue retention volume;
   a suction port in fluid communication with the filtrate volume and configured to access the filtrate volume for suctioning material from the filtrate volume;
   wherein, the internal containment volume includes a pellet well disposed in a bottom portion of the filtrate volume below a bottom elevation of the filter and accessible only from above when the apparatus is in the access orientation.

2. An apparatus according to example implementation 1, comprising a tissue collector disposed in the tissue retention volume and rotatable relative to the container in at least a first direction of rotation about an axis of rotation, the tissue collector including at least one toothed member that sweeps through a portion of the tissue retention volume when the tissue collector is rotated in the first direction, the toothed member being configured with a plurality of teeth to collect and retain stringy tissue when the tissue collector is rotated in the first direction in contact with human biological material containing stringy tissue disposed in the tissue retention volume.

3. An apparatus according to example implementation 2, wherein each said toothed member includes at least three teeth and an open space between the teeth of each pair of adjacent said teeth.

4. An apparatus according to any one of example implementations 2-3, wherein the tissue collector comprises at least two of said toothed member.

5. An apparatus according to any one of example implementations 2-4, wherein each said toothed member has a first end located radially toward the axis and a second end located radially away from the axis, and wherein the second end is located from one to 10 centimeters from the axis.
6. An apparatus according to any one of example implementations 2-5, wherein the teeth project toward a leading side of the toothed member when the tissue collector is rotated in the first direction.
7. An apparatus according to any one of example implementations 2-6, wherein the teeth project in a plane of rotation of the toothed member when the tissue collector is rotated in the first direction.
8. An apparatus according to any one of example implementations 2-7, wherein each of the teeth has a height of from 1 millimeter to 10 millimeters relative to a bottom of each adjacent said open space.
9. An apparatus according to any one of example implementations 2-8, comprising a first mixing impeller in the tissue retention volume.
10. An apparatus according to example implementation 9, wherein the first mixing impeller is configured to direct axial flow from the first mixing impeller in a direction toward the tissue collector.
11. An apparatus according to either one of Claim 9 or example implementation 10, wherein the first mixing impeller includes at least one portion configured to scrape a portion of the filter when the first mixing impeller is operated.
12. An apparatus according to example implementation 11, wherein each said portion of the first mixing impeller configured to scrape a portion of the filter includes a peripheral edge portion of an impeller blade of the first mixing impeller.
13. An apparatus according to either one of example implementation 11 or example implementation 12, wherein at least a part of each said portion of the filter is in a tapered portion of the filter that is disposed in a tapered portion of the internal containment volume.
14. An apparatus according to any one of example implementations 9-13, wherein the tissue collector and the first mixing impeller are coaxial and rotatable about the axis in the first direction.
15. An apparatus according to example implementation 14, wherein a spacing along the axis between the first mixing impeller and the tissue collector is in a range of from 0.5 centimeter to 5 centimeters.
16. An apparatus according to any one of example implementations 9-14, wherein the first mixing impeller extends to a first radial distance from the axis and the tissue collector extends to a second radial distance from the axis, wherein the second radial distance is larger than the first radial distance by at least 1 millimeter.
17. An apparatus according to any one of example implementations 9-16, comprising a second mixing impeller in the tissue retention volume.
18. An apparatus according to example implementation 17, wherein the second mixing impeller is configured to direct axial flow in a direction away from the tissue collector when the rotatable shaft is rotated in the first direction.
19. An apparatus according to either one of example implementation 17 or example implementation 18, wherein the tissue collector and the second mixing impeller are coaxial and rotatable about the axis in the first direction.
20. An apparatus according to example implementation 19, wherein a spacing along the axis between the second mixing impeller and the tissue collector is in a range of from 0.5 centimeter to 5 centimeters.
21. An apparatus according to any one of example implementations 17-20, wherein the second mixing impeller extends to a third radial distance from the axis that is at least 1 millimeter smaller than a radial distance from the axis to which the tissue collector extends.
22. An apparatus according to any one of example implementations 1-21, wherein the apparatus is orientable in a first orientation in which the inlet port and the outlet port are configured for access therethrough from above the container into the internal containment volume.
23. An apparatus according to example implementation 22, wherein in the first orientation, all access to the internal containment volume is from above the container.
24. An apparatus according to example implementation 22 or example implementation 23, comprising an extraction port configured for accessing the internal containment volume to remove processed biological material from the internal containment volume; and
wherein the extraction port is configured for access therethrough from above the container into the internal containment volume when the apparatus is oriented in the first orientation.
25. An apparatus according to example implementation 24, wherein access through the extraction port is through a lumen extending through the rotatable shaft aligned with the axis.
26. An apparatus according to example implementation 24, wherein no access is provided into the internal containment volume through a lumen extending through a rotatable shaft.
27. An apparatus according to any one of example implementations 1-26, wherein the filter has a separation size in a range of from 70 to 400 microns.
28. An apparatus according to any one of example implementations 1-26, wherein the filter has a separation size that is larger than 400 microns and not larger than 800 microns.
29. An apparatus according to any one of example implementations 1-28, wherein the container is configured to be received in a centrifuge for centrifuging the container.
30. An apparatus according any one of example implementations 1-29, wherein the internal containment volume has a volume in a range of from 100 cubic centimeters to 1300 cubic centimeters.
31. An apparatus according to any one of example implementations 1-30, wherein:
the filtrate volume includes a lower tapered portion below a bottom elevation of the filter and above a top elevation of the pellet well;
the lower tapered portion of the filtrate volume is defined by internal wall surfaces of the container that are each inclined relative to horizontal at a maximum angle of no larger than 60° when the container is in an access orientation;
at least a portion of the pellet well is defined by a wall surface of the container inclined relative to horizontal at an angle that is larger than the maximum angle of the lower tapered portion when the apparatus is in the access orientation.
32. An apparatus according to example implementation 31, wherein the wall surface of the container defining at least a portion of the pellet well is inclined relative to horizontal at an angle of at least 70° when the apparatus is in the access orientation.

33. An apparatus according to either one of example implementation 31 or example implementation 32, wherein:
when the apparatus is in the access orientation, the pellet well has at least one portion with a vertical length of 0.5 centimeter, a maximum horizontal cross-dimension of no larger than 10 millimeters and a minimum horizontal cross-dimension of no smaller than 1.5 millimeters.

34. An apparatus according to any one of example implementations 31-33, wherein the pellet well has a volume in a range of from 0.5 cubic centimeter to 2 cubic centimeters.

35. An apparatus according to any one of example implementations 31-34, wherein the internal containment volume includes an available processing volume in a range of from 300 cubic centimeters to 400 cubic centimeters.

36. An apparatus according to any one of example implementations 31-35, wherein the lower tapered portion includes a frustoconical portion with an angle of taper relative to horizontal in a range of from 42° to 48° when the container is in the access orientation.

37. An apparatus according to any one of example implementations 31-36, wherein the pellet well includes a frustoconical portion with an angle of taper relative to horizontal of at least 70° when the container is in the access orientation.

38. An apparatus according to any one of example implementations 31-37, wherein when the portable container apparatus is in the access orientation the internal containment volume comprises:
a first portion that is cylindrical or is frustoconical tapering toward the bottom of the internal containment volume with an angle of taper relative to horizontal of at least 70°;
a second portion disposed below the first portion, the second portion being frustoconical tapering toward the bottom of the internal containment volume with an angle of taper relative to horizontal in a range of from 30° to 60°;
a third portion disposed below the second portion in the pellet well, the third portion being cylindrical or frustoconical tapering toward the bottom of the internal containment volume at an angle of taper relative to horizontal of at least 70°.

39. A method of processing adipose tissue using an apparatus according to any one of example implementations 1-38, the method comprising processing in the container of the apparatus, the processing comprising:
washing adipose tissue within the container to remove contaminants from the adipose tissue.

40. A method according to example implementation 39, comprising after the washing, removing washed adipose tissue from the container.

41. A method according to example implementation 39, comprising;
after the washing, digesting adipose tissue within the container, the digesting adipose tissue comprising adding to the container a volume of enzyme-containing digestion medium to contact washed adipose tissue in the container;
after permitting enzymatic digestion in the container for a retention time following adding the digestion medium, disposing the container in a centrifuge and centrifuging the container in the centrifuge to form density-separated phases within the container, the density-separated phases including lower-density material phases and a higher-density pellet phase comprising leuko stromal vascular cells; and
selectively removing material of the pellet phase from the container.

42. A method according to example implementation 41, wherein the selectively removing comprises:
inserting an aspiration tube from outside of to inside of the container to contact the pellet phase inside the container; and
aspirating at least a majority of material of the pellet phase through the aspiration tube to outside of the container without suspending material of the pellet phase in a suspension liquid in the container.

43. A method according to example implementation 42, wherein:
the lower-density material phases include an aqueous phase above the pellet phase; and
the aqueous phase is not removed from the container prior to the aspirating.

44. A method according to either one of example implementation 42 or example implementation 43, wherein after the aspirating, the lower-density material phases remain in the container.

45. A method according to any one of example implementations 42-44, wherein the inserting comprises inserting the aspiration tube downward into the container from above.

46. A method according to any one of example implementations 42-45, wherein:
the aspirating comprises aspirating the at least a majority of the material of the pellet phase into a receptacle located outside of the container that is in fluid communication with the aspiration tube; and
prior to commencement of the aspirating, the receptacle contains a volume of dispersion medium and during the aspirating the dispersion medium mixes with the at least a majority of the material of the pellet phase in the receptacle.

47. A method according to example implementation 46, wherein the volume of the dispersion medium is in a range of from 2 times to 10 times a volume of the at least a majority of the material of the pellet phase that is aspirated into the receptacle during the aspirating.

48. A method according to any one of example implementations 42-47, wherein during the aspirating the aspiration tube is in fluid communication with a syringe and the aspirating comprises collecting the at least a majority of the material of the pellet phase into the syringe.

49. A method according to example implementation 39, wherein:
the washing comprises multiple wash cycles with each said wash cycle comprises:
adding a volume of aqueous wash liquid to the container to contact the adipose tissue within the container;
mixing the wash liquid and the adipose tissue in the container; and
removing at least a majority of the wash liquid with contaminants from the filtrate volume of the container on a first side of the filter and retaining at least most of the adipose tissue in the tissue retention volume of the container disposed on a second side of the filter;

and the method further comprises:

after the washing, digesting adipose tissue within the container, the digesting adipose tissue comprising:

adding to the container a volume of digestion medium comprising a collagenase enzyme solution to contact washed adipose tissue in the container following the washing, wherein a volume ratio of the volume of digestion medium to volume of adipose tissue within the container is in a range of from 0.6:1 to 2:1 and where the digestion medium provides from 150 to 300 collagen digestion units (CDU) per milliliter of catalytic volume, wherein the catalytic volume is the total of the volume of digestion medium and the volume of adipose tissue within the container; and after the adding of the volume of digestion medium, permitting enzymatic digestion within the container for a retention time in a range of from 20 minutes to 50 minutes while the container is disposed in a temperature controlled environment maintained within a temperature range of from 32° C. to 38° C. and with at least occasional agitation of contents within the container; and not later than 50 minutes following the adding of the volume of digestion medium, adding a stopping reagent to the container to stop enzymatic activity within the container;

disposing the container in a centrifuge and centrifuging the container in the centrifuge to form density-separated phases within the container, the density-separated phases including lower-density material phases and a higher-density pellet phase comprising leuko stromal vascular cells;

after the centrifuging, removing the container from the centrifuge; and removing the lower-density material phases from the container while retaining the pellet phase within the container.

50. An apparatus for processing human biological material, for example which processing may include preparation of a cell concentrate, which human biological material may or may not contain stringy tissue, the apparatus being orientable in an access orientation and the apparatus comprising;

a container having an internal containment volume, the internal containment volume including a tissue retention volume and a filtrate volume;

a filter disposed within the internal containment volume with the tissue retention volume on one side of the filter and the filtrate volume on another side of the filter with the tissue retention volume and with the filtrate volume being in fluid communication through the filter;

an inlet port in fluid communication with the tissue retention volume and configured to access the tissue retention volume for introducing human biological material into the tissue retention volume;

a suction port in fluid communication with the filtrate volume and configured to access the filtrate volume for suctioning material from the filtrate volume;

wherein:

the internal containment volume includes a pellet well disposed in a bottom portion of the filtrate volume below a bottom elevation of the filter and accessible only from above when the apparatus is in the access orientation;

the filtrate volume includes a lower tapered portion below a bottom elevation of the filter and above a top elevation of the pellet well when the apparatus is in the access orientation;

the lower tapered portion of the filtrate volume is defined by internal wall surfaces of the container that are each inclined relative to horizontal at a maximum angle of no larger than 60° when the container is in the access orientation; and at least a portion of the pellet well is defined by a wall surface of the container inclined relative to horizontal at an angle that is larger than the maximum angle of the lower tapered portion when the apparatus is in the access orientation.

51. An apparatus according to example implementation 50, wherein the wall surface of the container defining at least a portion of the pellet well is inclined relative to horizontal at an angle of at least 70° when the apparatus is in the access orientation.

52. An apparatus according to either one of example implementation 50 or example implementation 51, wherein:

when the apparatus is in the access orientation, the pellet well has at least one portion with a vertical length of 0.5 centimeter, a maximum horizontal cross-dimension of no larger than 10 millimeters and a minimum horizontal cross-dimension of no smaller than 1.5 millimeters.

53. An apparatus for processing human biological material, for example which processing may include preparation of a cell concentrate, which human biological material may or may not contain stringy tissue, the apparatus being orientable in an access orientation and the apparatus comprising;

a container having an internal containment volume, the internal containment volume including a tissue retention volume and a filtrate volume;

a filter disposed within the internal containment volume with the tissue retention volume on one side of the filter and the filtrate volume on another side of the filter with the tissue retention volume and with the filtrate volume being in fluid communication through the filter;

an inlet port in fluid communication with the tissue retention volume and configured to access the tissue retention volume for introducing human biological material into the tissue retention volume;

a suction port in fluid communication with the filtrate volume and configured to access the filtrate volume for suctioning material from the filtrate volume;

wherein:

the internal containment volume includes a pellet well disposed in a bottom portion of the filtrate volume below a bottom elevation of the filter and accessible only from above when the apparatus is in the access orientation; and when the apparatus is in the access orientation, the pellet well has at least one portion with a vertical length of 0.5 centimeter, a maximum horizontal cross-dimension of no larger than 10 millimeters and a minimum horizontal cross-dimension of no smaller than 1.5 millimeters.

54. An apparatus according to any one of example implementations 50-53, wherein the pellet well has a volume in a range of from 0.5 cubic centimeter to 2 cubic centimeters.

55. An apparatus according to any one of example implementations 50-54, wherein the internal containment volume has a maximum cross-section taken horizontally when the apparatus is in the access orientation that fits entirely within a circle having a diameter of not larger than 16 centimeters.
56. An apparatus according to any one of example implementations 50-55, wherein the internal containment volume is defined at least in part by a shell having a lip and a portion to be disposed in a centrifuge receptacle during centrifuge processing, the portion of the shell to be disposed in a centrifuge being below the lip when the apparatus is in the access orientation; and
when the apparatus is in the access orientation, the portion of the shell below the lip to be disposed in a centrifuge has a maximum cross-section taken horizontally through the shell that fits entirely within a circle having a diameter of not larger than 16 centimeters.
57. An apparatus according to example implementation 56, wherein the portion of the shell below the lip to be disposed in a centrifuge has a height dimension when the apparatus is in the access orientation in a range of from 2 centimeters to 16 centimeters.
58. An apparatus according to example implementation 56 or example implementation 57, wherein the maximum cross-section of the portion of the shell below the lip to be disposed in a centrifuge is circular.
59. An apparatus according to any one of example implementations 50-58, comprising total height when in the access orientation in a range of from 3 to 26 centimeters.
60. An apparatus according to any one of example implementations 50-59, wherein the internal containment volume comprises an available processing volume in a range of from 5 cubic centimeters to 1300 cubic centimeters, with a portion of the available processing volume being in the tissue retention volume.
61. An apparatus according to example implementation 60, wherein the available processing volume is in a range of from 5 cubic centimeters to 400 cubic centimeters.
62. An apparatus according to example implementation 60, wherein the available processing volume is in a range of from 300 cubic centimeters to 400 cubic centimeters.
63. An apparatus according to any one of example implementations 60-62, wherein the portion of the available processing volume in the tissue retention volume is in a range of from 40 percent to 60 percent of the available processing volume.
64. An apparatus according to any one of example implementations 60-63, wherein the portion of the available processing volume in the tissue retention volume is in a range of from 45 percent to 55 percent of the available processing volume.
65. An apparatus according to any one of example implementations 60-64, wherein the pellet well has a volume in a range of from 0.2 percent to 2 percent of the portion of the available processing volume in the tissue retention volume.
66. An apparatus according to any one of example implementations 60-65, wherein the pellet well has a volume in a range of from 0.3 percent to 1.5 percent of the portion of the available processing volume in the tissue retention volume.
67. An apparatus according to any one of example implementations 50-66, wherein the lower tapered portion includes a frustoconical portion with an angle of taper relative to horizontal in a range of from 42° to 48° when the container is in the access orientation.
68. An apparatus according to any one of example implementations 50-67, wherein the pellet well includes a frustoconical portion with an angle of taper relative to horizontal of at least 70° when the container is in the access orientation.
69. An apparatus according to any one of example implementations 50-68, wherein when the portable container apparatus is in the access orientation the internal containment volume comprises:
a first portion that is cylindrical or is frustoconical tapering toward the bottom of the internal containment volume with an angle of taper relative to horizontal of at least 70°;
a second portion disposed below the first portion, the second portion being frustoconical tapering toward the bottom of the internal containment volume with an angle of taper relative to horizontal in a range of from 30° to 60°;
a third portion disposed in the pellet well and below the second portion, the third portion being cylindrical or frustoconical tapering toward the bottom of the internal containment volume at an angle of taper relative to horizontal of at least 70°.
70. An apparatus according to any one of example implementations 50-69, comprising a tissue collector disposed in the tissue retention volume and rotatable relative to the container in at least a first direction of rotation about an axis of rotation of a rotatable shaft, the tissue collector including at least one toothed member that sweeps through a portion of the tissue retention volume when the tissue collector is rotated in the first direction, the toothed member being configured with a plurality of teeth to collect and retain stringy tissue when the tissue collector is rotated in the first direction in contact with human biological material containing stringy tissue disposed in the tissue retention volume.
71. An apparatus according to example implementation 70, wherein each said toothed member has a first end located radially toward the axis and a second end located radially away from the axis, each said toothed member includes between the first end and the second end at least three teeth and an open space between the teeth of each pair of adjacent said teeth and the teeth project toward a leading side of the toothed member when the tissue collector is rotated in the first direction.
72. An apparatus according to any one of example implementations 50-71, wherein in the access orientation, all access to the internal containment volume is from above the container.
73. A method of processing adipose tissue using an apparatus according to any one of example implementations 50-72, the method comprising processing in the container of the apparatus, the processing comprising:
washing adipose tissue within the container to remove contaminants from the adipose tissue;
after the washing, digesting adipose tissue within the container, the digesting adipose tissue comprising adding to the container a volume of enzyme-containing digestion medium to contact washed adipose tissue in the container;
after permitting enzymatic digestion in the container for a retention time following adding the digestion medium, disposing the container in a centrifuge and centrifuging the container in the centrifuge to form density-separated phases within the container, the density-separated phases including lower-density material phases and a higher-density pellet phase comprising leuko stromal vascular cells; and selectively removing material of the pellet phase from the container, the selectively removing comprising:

inserting an aspiration tube from outside of to inside of the container to contact the pellet phase inside the container; and aspirating at least a majority of material of the pellet phase through the aspiration tube to outside of the container without suspending material of the pellet phase in a suspension liquid in the container.

74. A method for removing pellet phase material from an apparatus according to any one of example implementations 50-73, wherein the container of the apparatus contains density-separated phases from centrifuging following enzymatic digestion of human biological material, the density-separated phases comprise lower-density material phases and a higher-density pellet phase, the method comprising selectively removing material of the pellet phase from the container of the apparatus, wherein the selectively removing comprises:

inserting an aspiration tube from outside of to inside of the container to contact the pellet phase inside the container; and aspirating at least a majority of material of the pellet phase through the aspiration tube to outside of the container without suspending material of the pellet phase in a suspension liquid in the container.

75. A method according to either one of example implementation 73 or example implementation 74, wherein:

the lower-density material phases include an aqueous phase above the pellet phase; and the aqueous phase is not removed from the container prior to the aspirating.

76. A method according to any one of example implementations 73-75, wherein after the aspirating, the lower-density material phases remain in the container.

77. A method according to any one of example implementations 73-76, wherein the inserting comprises inserting the aspiration tube downward into the container from above.

78. A method according to any one of example implementations 73-77, wherein:

the aspirating comprises aspirating the at least a majority of the material of the pellet phase into a receptacle located outside of the container that is in fluid communication with the aspiration tube; and prior to commencement of the aspirating, the receptacle contains a volume of dispersion medium and during the aspirating the dispersion medium mixes with the at least a majority of the material of the pellet phase in the receptacle.

79. A method according to example implementation 78, wherein the volume of the dispersion medium is in a range of from 2 times to 10 times a volume of the at least a majority of the material of the pellet phase that is aspirated into the receptacle during the aspirating.

80. A method according to any one of example implementations 73-79, wherein during the aspirating the aspiration tube is in fluid communication with a syringe and the aspirating comprises collecting the at least a majority of the material of the pellet phase into the syringe.

The foregoing discussion of the invention and different aspects thereof has been presented for purposes of illustration and description. The foregoing is not intended to limit the invention to only the form or forms specifically disclosed herein. Consequently, variations and modifications commensurate with the above teachings, and the skill or knowledge of the relevant art, are within the scope of the present invention. The embodiments described hereinabove are further intended to explain best modes known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art. Although the description of the invention has included description of one or more possible implementations and certain variations and modifications, other variations and modifications are within the scope of the invention, e.g., as may be within the skill and knowledge of those in the art after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter. Furthermore, any feature described or claimed with respect to any disclosed implementation may be combined in any combination with one or more of any other features of any other implementation or implementations, to the extent that the features are not necessarily technically compatible, and all such combinations are within the scope of the present disclosure.

The terms "comprising", "containing", "including" and "having", and grammatical variations of those terms, are intended to be inclusive and nonlimiting in that the use of such terms indicates the presence of some condition or feature, but not to the exclusion of the presence also of any other condition or feature. The use of the terms "comprising", "containing", "including" and "having", and grammatical variations of those terms in referring to the presence of one or more components, subcomponents or materials, also include and is intended to disclose the more specific embodiments in which the term "comprising", "containing", "including" or "having" (or the variation of such term) as the case may be, is replaced by any of the narrower terms "consisting essentially of" or "consisting of" or "consisting of only" (or the appropriate grammatical variation of such narrower terms). For example, a statement that some thing "comprises" a stated element or elements is also intended to include and disclose the more specific narrower embodiments of the thing "consisting essentially of" the stated element or elements, and the thing "consisting of" the stated element or elements. Examples of various features have been provided for purposes of illustration, and the terms "example", "for example" and the like indicate illustrative examples that are not limiting and are not to be construed or interpreted as limiting a feature or features to any particular example. The term "at least" followed by a number (e.g., "at least one") means that number or more than that number. The term at "at least a portion" means all or a portion that is less than all. The term "at least a part" means all or a part that is less than all. Operations or steps of any method or process need not be performed in any particular order unless a particular order is required.

What is claimed is:

1. A method for making a product comprising a delivery composition for administration to a human patient of uncultured stromal vascular fraction cells derived from harvested adipose tissue from the patient, the method comprising:

washing a volume of harvested adipose tissue from the patient within a single-use, portable processing container to prepare washed adipose tissue within the processing container;

after the washing, enzymatically digesting the washed adipose tissue within the processing container, the enzymatically digesting comprising;

preparing a process mixture in the processing container, comprising adding an enzyme-containing digestion medium to the processing container to contact the washed adipose tissue; and agitating the process mixture to release stromal vascular fraction cells from the washed adipose tissue;

after a retention time following the adding, centrifuging the processing container to form in the processing container a density-separated pellet phase of stromal vascular fraction cell concentrate comprising stromal vascular fraction cells released from the washed adipose tissue during the enzymatically digesting;

after the centrifuging, selectively removing at least a portion of the stromal vascular fraction cell concentrate from the processing container; and disposing in a syringe a delivery composition comprising a volume of 0.25 milliliter to 2.5 milliliters of the stromal vascular fraction cell concentrate removed from the processing container dispersed in a dispersion medium suitable for administration to the patient.

2. The method of claim 1, wherein the delivery composition comprises a ratio of a volume of the dispersion medium to the volume of the stromal vascular fraction in a range of from 1:1 to 10:1.

3. The method of claim 1, wherein the delivery composition comprises a volume of the dispersion medium in a range of from 1 milliliter to 10 milliliters.

4. The method of claim 1, wherein the volume of the harvested adipose tissue is in a range of from 20 cubic centimeters to 175 cubic centimeters.

5. The method of claim 1, wherein the centrifuging comprises centrifuging the processing container until the pellet phase of the stromal vascular fraction cell concentrate has a volume in a range of from 0.2 percent to 2 percent of the volume of the harvested adipose tissue.

6. The method of claim 1, wherein the agitating comprises moving mixing blades through the process mixture in the processing container.

7. The method of claim 6, wherein the processing container comprises:

an internal containment volume including a tissue retention volume and a filtrate volume;

a filter disposed within an internal containment volume with the tissue retention volume on one side of the filter and the filtrate volume on another side of the filter, with the tissue retention volume and the filtrate volume being in fluid communication through the filter; and a rotatable mixer, comprising the mixing blades, disposed in the tissue retention volume;

and wherein:

at commencement of the washing the volume of the harvested adipose tissue is disposed in the tissue retention volume and following the washing and at commencement of the enzymatically digesting, the washed adipose tissue is disposed in the tissue retention volume; and the washing comprises rotating the rotatable mixer in the tissue retention volume to mix adipose tissue and wash liquid in the tissue retention volume.

8. The method of claim 7, wherein the centrifuging comprises centrifuging the processing container until the pellet phase of the stromal vascular fraction cell concentrate has a volume in a range of from 0.2 percent to 2 percent of the volume of the harvested adipose tissue.

9. The method of claim 8, wherein the selectively removing comprises aspirating at least the volume of the stromal vascular fraction cell concentrate directly from the pellet phase through an aspiration tube into a fluid receptacle located outside of the processing container.

10. The method of claim 9, wherein:

during the aspirating the aspiration tube extends through a vertical portion of the filtrate volume, with the vertical portion having a vertical length of at least 0.5 centimeter, a maximum horizontal cross-dimension of no larger than 10 millimeters and a minimum horizontal cross-dimension of no smaller than 1.5 millimeters; and at least a portion of the pellet phase aspirated through the aspiration tube during the aspirating is disposed in the vertical portion at commencement of the aspirating.

11. The method of claim 10, wherein the fluid receptacle is pre-loaded with a quantity of the dispersion medium that is present in the fluid receptacle during the aspirating.

12. The method of claim 11, wherein the volume of the dispersion medium is in a range of from 1 milliliter to 10 milliliters and the delivery composition in the syringe comprises a ratio of a volume of the dispersion medium to the volume of the stromal vascular fraction in a range of from 1:1 to 10:1.

13. The method of claim 12, comprising:

prior to the washing, performing a lipoplasty procedure on the patient to obtain the harvested adipose tissue from the patient in lipoaspirate;

during the lipoplasty procedure, collecting at least the volume of the harvested adipose tissue in the tissue retention volume of the processing container, wherein the collecting comprises introducing into the tissue retention volume a quantity of the lipoasperate comprising at least the volume of the harvested adipose tissue.

14. The method of claim 13, wherein the volume of the harvested adipose tissue is in a range of from 20 cubic centimeters to 175 cubic centimeters.

15. The method of claim 1, wherein after the centrifuging, the method is in the absence of suspending the volume of the stromal vascular fraction cell concentrate in a suspension liquid in the processing container.

16. The method of claim 1, wherein the selectively removing comprises aspirating at least the volume of the stromal vascular fraction cell concentrate directly from the pellet phase through an aspiration tube into a fluid receptacle located outside of the processing container.

17. The method of claim 16, wherein:

the delivery composition comprises a volume of the dispersion medium; and the fluid receptacle is pre-loaded with at least the volume of the dispersion medium that is present in the fluid receptacle during the aspirating.

18. The method of claim 16, wherein;

the centrifuging comprises preparing multiple density-separated phases in the processing container, the multiple density-separated phases including lower-density material phases above the pellet phase; and the aspirating is performed without first removing the lower-density material phases from the processing container.

19. The method of claim 16, wherein the selectively removing comprises:
inserting the aspiration tube from outside to inside the processing container and downwardly inside the processing container into the pellet phase.

20. The method of claim 16, wherein:
during the aspirating the aspiration tube extends through a vertical portion of an internal containment volume of the processing container, with the vertical portion having a vertical length of at least 0.5 centimeter, a maximum horizontal cross-dimension of no larger than 10 millimeters and a minimum horizontal cross-dimension of no smaller than 1.5 millimeters; and
at least a portion of the pellet phase aspirated through the aspiration tube during the aspirating is disposed in the vertical portion at commencement of the aspirating.

* * * * *